US007982022B2

(12) United States Patent
Russell et al.

(10) Patent No.: US 7,982,022 B2
(45) Date of Patent: Jul. 19, 2011

(54) SYSTEM FOR MONITORING THE LOCATION OF TRANSGENES

(75) Inventors: Stephen J. Russell, Rochester, MN (US); John Morris, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/638,435

(22) Filed: Dec. 15, 2009

(65) Prior Publication Data
US 2010/0099182 A1 Apr. 22, 2010

Related U.S. Application Data

(60) Division of application No. 10/428,868, filed on May 1, 2003, now Pat. No. 7,645,865, which is a continuation of application No. 09/640,198, filed on Aug. 16, 2000, now Pat. No. 6,586,411.

(51) Int. Cl.
C07H 21/02 (2006.01)
C12Q 1/68 (2006.01)
C12N 15/00 (2006.01)
(52) U.S. Cl. ............ 536/23.1; 435/6; 435/320.1
(58) Field of Classification Search ............ 435/320.1, 435/6; 536/23.1
See application file for complete search history.

(56) References Cited

U.S. PATENT DOCUMENTS

| 4,108,983 | A | 8/1978 | Wallack |
| 4,500,512 | A | 2/1985 | Barme |
| 4,985,244 | A | 1/1991 | Makino et al. |
| 5,001,692 | A | 3/1991 | Farla et al. |
| 5,137,727 | A | 8/1992 | Eckenhoff |
| 5,262,359 | A | 11/1993 | Hierholzer |
| 5,304,367 | A | 4/1994 | Biegon |
| 5,631,237 | A | 5/1997 | Dzau et al. |
| 5,661,032 | A | 8/1997 | Miller et al. |
| 5,703,056 | A | 12/1997 | Blasberg et al. |
| 5,713,858 | A | 2/1998 | Heruth et al. |
| 5,738,985 | A | 4/1998 | Miles et al. |
| 5,980,508 | A | 11/1999 | Cardamone et al. |
| 6,012,034 | A | 1/2000 | Hamparian et al. |
| 6,026,316 | A | 2/2000 | Kucharczyk et al. |
| 6,083,751 | A | 7/2000 | Feldhaus et al. |
| 6,095,976 | A | 8/2000 | Nachtomy et al. |
| 6,110,461 | A | 8/2000 | Lee et al. |
| 6,391,579 | B1 | 5/2002 | Carrasco et al. |
| 6,440,419 | B1 | 8/2002 | Hein et al. |
| 2003/0118553 | A1 * | 6/2003 | Petrich et al. ............ 424/93.2 |

FOREIGN PATENT DOCUMENTS

| WO | WO 97/12032 | 4/1997 |
| WO | WO 97/12048 | 4/1997 |
| WO | WO 9845443 A1 * | 10/1998 |
| WO | WO 99/60135 | 11/1999 |
| WO | WO 00/76450 | 6/2000 |

OTHER PUBLICATIONS

Bateman A, et al. Fusogenic membrane glycoproteins as a novel class of genes for the local and immune-mediated control of tumor growth. Cancer Res., vol. 60, pp. 1492-1497, 2000.*
Stratagene Catalog. Gene Characterization kits. Stratage Catalog, pp. 39, 1988.*
GenBank Accession No. U60282, Nature, vol. 379 (6564), pp. 458-460, 1996.
Abai et al., "Insulin delivery with plasmid DNA," Hum. Gene Ther., 1999, 10(16)2637-2649.
Albonico et al., "Febrile infectious childhood diseases in the history of cancer patients and matched controls," Medical Hypotheses, 1998, 51:315-320.
Alemany et al., "Replicative adenoviruses for cancer therapy," Nature Biotechnology,2000, 18:723-727.
Anderson, "Human gene therapy," Nature, 1998, 392(Supp.):25-30.
Andreansky et al., "The application of genetically engineered herpes simplex viruses to the treatment of experimental brain tumors," Proc. Natl. Acad. Sci. USA, 1996, 93:11313-11318.
Appelos et al., "Activation peptide of carboxypeptidase B in serum and urine in acute pancreatitis," Gut, 1998, 42;97-102.
Arbit et al., "Quantitative studies of monoclonal antibody targeting to disialoganglioside $G_{D2}$ in human brain tumors," Eur. J. Nucl. Med., 1995, 22:419-426.
Asada, "Treatment of Human Cancer with Mumps Virus," Cancer, 1974, 34:1907-1928.
Bae et al., "Genomic Differences between the Diabetogenic and Nondiabetogenic Variants of Encephalomyocarditis Virus," Virology, 1989, 170:282-287.
Bateman et al., "Fusogenic Membrane Glycoproteins—A Novel Class of Cytotoxic Genes with Immunostimulatory Properties," Gene Therapy, 1999, 6(Suppl. 1):56, Abstract #24.
Bateman et al., "Fusogenic Membrane Glycoproteins As a Novel Class of Genes for the Local and Immune-mediated Control of Tumor Growth," Cancer Research, 2000, 60:1492-1497 (Correction published 2000, 1 page).
Bennett et al., "Fusion of Green Fluorescent Protein with the Zeocin™-Resistance Marker Allows Visual Screening and Drug Selection of Transfected Eukaryotic Cells," BioTechniques, 1998, 24(3):478-482.
Berg et al., "Physiological functions of endosomal proteolysis," Biochem. J., 1995, 307:313-326.
Bluming and Ziegler, "Regression of Burkitt's Lymphoma in Association with Measles Infection," Lancet, 1971, pp. 105-106.

(Continued)

Primary Examiner — Suryaprabha Chunduru
(74) Attorney, Agent, or Firm — Fish & Richardson P.C.

(57) ABSTRACT

A novel strategy for monitoring the location of a transgene in a mammal is disclosed. A sodium iodide symporter is genetically fused to either the N-terminus or C-terminus of the product of a transgene through a linker peptide which bears the recognition sequence of a host cell protease. Expression of the transgene confers the activity of the sodium iodide symporter (NIS) to a host cell which expresses the transgene. Subsequent administration of labeled iodine results in transport of the labeled iodine into the cell bearing the NIS, which can then be localized and measured using standard imaging techniques. The system is particularly useful for monitoring the location of therapeutic transgenes and tissue-specific distribution of the therapeutic gene product.

6 Claims, 9 Drawing Sheets

OTHER PUBLICATIONS

Bolt and Pedersent, "The Role of Subtilisin-like Proprotein Convertases for Cleavage of the Measles Virus Fusion Glycoprotein in Different Cell Types," *Virology*, 1998, 252:387-398.

Cathomen et al., "Measles Viruses with Altered Envelope Protein Cytoplasmic Tails Gain Cell Fusion Competence," *J. Virol.*, 1998, 72(2):1224-1234.

Cathomen et al., "A matrix-less measles virus is infectious and elicits extensive cell fusion: consequences for propagation in the brain," *EMBO J.*, 1998, 17(14):3899-3908.

Chambers et al., "Comparison of genetically engineered herpes simplex viruses for the treatment of brain tumors in a *scid* mouse model of human malignant glioma," *Proc. Natl. Acad. Sci. USA*, 1995, 92:1411-1415

Ch'ien et al., "Fatal Subacute Immunosuppressive Measles Encephalitis (SIME) in Children with Acute Lymphcytic Leukemia—Clinical, Electroencephalographic, and Computerized Tomographic Scan Features," *Clin. Electroencephalogr.*, 1983, 14(4):214-220.

Cleutjens, K.B.J.M. et al, "A 6-kb promoter fragment mimics in transgenic mice the prostate-specific and androgen-regulated expression of the endogenous prostate-specific antigen gene in humans," *Molecular Endocrinology*, 1997, 11:1256-1265.

Cohen et al., "Complete nucleotide sequence of an attenuated hepatitis A virus: Comparison with wild-type virus," *Proc. Natl. Acad. Sci. USA*, 1987, 84:2497-2501.

Crawford et al., "Thyroid volume measurement in thyrotoxic patients: comparison between ultrasonography and iodine-124 positron emission tomography," *Eur. J. Nucl. Med.*, 1997, 24:1470-1478.

Dai et al., "Cloning and characterization of the thyroid iodide transporter," *Nature*, 1996, 379:458-460.

de Felipe et al., "Use of the 2A sequence from foot-and-mouth disease virus in the generation of retroviral vectors for gene therapy," *Gene Ther.*, 1999, 6:198-208.

Delassus et al., "Genetic Organization of Gibbon Ape Leukemia Virus," *Virology*, 1989, 173:205-213.

de Swart et al., "Measles in a Dutch hospital introduced by an immuno-compromised infant from Indonesia infected with a new virus genotype," *Lancet*, 2000, 355:201-202.

Douglass et al., "Polyprotein Gene Expression; Generation of Diversity of Neuroendocrine Peptides," *Ann. Rev. Biochem.*, 1984, 53:665-715.

Duechler et al., "Evolutionary relationships within the human rhinovirus genus: Comparison of serotypes 89, 2, and 14," *Proc. Natl. Acad. Sci. USA*, 1987, 84:2605-2609.

Duprex et al., "Observation of Measles Virus Cell-to-Cell Spread in Astrocytoma Cells by Using a Green Fluorescent Protein-Expressing Recombinant Virus," *J. Virol.*, 1999, 73(11):9568-9575.

Earle et al., "The Complete Nucleotide Sequence of a Bovine Enterovirus," *J. Gen. Virol.*, 1988, 69:253-263.

Eiselein et al., "Treatment of Transplanted Murine Tumors with an Oncolytic Virus and Cyclophosphamide," *Cancer Res.*, 1978, 38:3817-3822.

Evermann and Burnstein, "Immune Enhancement of the Tumorigenicity of Hamster Brain Tumor Cells Persistently Infected with Measles Virus," *Int. J. Cancer*, 1975, 16:861-869.

Flower et al., "Thyroid imaging using position emission tomography—a comparison with ultrasound imaging and conventional scintigraphy in thyrotoxicosis," *Br. J. Radiol.*, 1990, 63:325-330.

Flower et al., "Dose-response study on thyrotoxic patients undergoing positron emission tomography and radioiodine therapy," *Eur. J. Nucl. Med.*, 1994, 21:531-536.

Fusogenic membrane glycoproteins as a novel class of genes for the local and immune-mediated control of tumor growth, *Cancer Res.*, 2000, 60:1492-1497.

Galanis et al., "Use of Fusogenic Membrane Glycoproteins as Novel Therapeutic Transgenes in Gliomas," *Gene Therapy*, 1999, 6(S1):S7, Abstract #28.

Gambhir et al., "Assays for Noninvasive Imaging of Reporter Gene Expression," *Nucl. Med. Biol.*, 1999, 26:481-490.

Greentree, "Hodgkin's Disease: Therapeutic Role of Measles Vaccine," *Am. J. Med.*, 1983, 75:928.

Gromeier et al., "Intergeneric poliovirus recombinants for the treatment of malignant glioma," *Proc. Natl. Acad. Sci. USA*, 2000, 97(12):6803-6808.

Grote et al., "Live attenuated measles virus induces regression of human lymphoma xenografts in immunodeficient mice," *Blood*, 2001, 97(12):3746-3754.

Gura, "Systems for Identifying New Drugs Are Often Faulty," *Science*, 1997, 278:1041-1042.

Hook, *Proteolytic and Cellular Mechanisms in Prohormone and Proprotein Processing*, 1998, R.G. Landes Company, Austin, Texas, (TOC only).

Hooper et al., "Membrane protein secretases," *Biochem. J.*, 1997, 321:265-279.

Hughes et al., "The Complete Nucleotide Sequence of Coxsackievirus A21," *J. Gen. Virol.*, 1989, 70:2943-2952.

Hutton, "Insulin secretory granule biogenesis and the proinsuilin-processing endopeptidases," *Diabetologia*, 1994, 37(Suppl. 2):S48-S56.

Iizuka et al., "Complete Nucleotide Sequence of the Genome of Coxsackievirus B1," *Virology*, 1987, 156:64-73.

Inchauspe et al., "Genomic structure of the human prototype strain H of hepatitis C virus: Comparison with American and Japanese isolates," *Biochem.*, 1991, 88:10292-10296.

Jackson, "Initiation without an end," *Nature*, 1991, 353:14-15.

Jenkins et al., "The Complete Nucleotide Sequence of Coxsackievirus B4 and Its Comparison to Other Members of the Picornaviridae," *J. Gen. Virol.*, 1987, 68:1835-1848.

Kao et al., "C-Peptide Immunochemiluminometric Assay Developed From Two Seemingly Identical Polyclonal Antisera," *Ann. Clin. Lab. Sci.*, 1992, 22(5):307-316, 348-350.

Kato et al., "Molecular cloning of the human hepatitis C virus genome from Japanese patients with non-A, non-B hepatitis," *Proc. Natl. Acad. Sci. USA*, 1990, 87:9524-9528.

Kenney and Pagano, "Viruses as Oncolytic Agents: a New Age for "Therapeutic" Viruses," *J. Natl. Cancer Inst.*, 1994, 86(16):1185-1186.

Kirn, "Replication-selective microbiological agents: fighting cancer with targeted germ warfare," *J. Clin. Invest.*, 2000, 105(7):837-839.

Kirn and McCormick, "Replicating viruses as selective cancer therapeutics," *Mol. Med. Today*, 1996, 2(12):519-527.

Kirn, "Replication-selective oncolytic adenoviruses: virotherapy aimed at genetic targets in cancer," *Oncogene*, 2000, 19:6660-6669.

Kuzumaki and Kobayashi, "Reduced Transplantability of Syngenic Mouse Tumors Superinfected with Membrane Viruses in NU/NU Mice," *Transplantation*, 1976, 22(6):545-550.

Linardakis et al., "Regulated Expression of Fusogenic Membrane Glycoproteins," *Gene Therapy*, 1999, 6(Suppl. 1):S4, Abstract #13.

Lorence et al., "Newcastle Disease Virus as an Antineoplastic Agent: Induction of Tumor Necrosis Factor-α and Augmentation of Its Cytotoxicity," *J. Nat. Cancer Inst.*, 1988, 80(16):1305-1312.

Lorence et al., Complete Regression of Human Neuroblastoma Xenografts in Athymic Mice After Local Newcastle Disease Virus Therapy,: *J. Natl. Cancer Inst.*, 1994, 86(16): 1228-1233.

Lynch and Snyder, "Neuropeptides: Multiple Molecular Forms, Metabolic Pathways, and Receptors," *Ann. Rev. Biochem.*, 1986, 55:773-799.

Macejak and Sarnow, "Internal initiation of translation mediated by the 5' leader of a cellular mRNA," *Nature*, 1991, 353:90-94.

Mazzaferri, "Radioiodine and other Treatments and Outcomes," *The Thyroid—A Fundamental and Clinical Text*, Braverman and Utiger (eds.), Seventh Edition, 1996, Lippincott—Raven Publishers, Philadelphia, pp. 922-945.

McMartin, "Molecular sieving, receptor processing and peptidolysis as major determinants of peptide pharmacokinetics in vivo," *Biochem. Society Transactions*, 1989, 17(5):931-934.

Mettler et al., "Virus Inoculation in Mice Bearing Ehrlich Ascitic Tumors: Antigen Production and Tumor Regression," *Infection and Immunity*, 1982, 37:23-27.

Mithöfer et al., "Quantitative Assay of Trypsinogen by Measurement of Cleaved Activation Peptide after Activation with Enterokinase," *Analytical Biochem.*, 1995, 230:348-350.

Mitus et al., "Attenuated Measles Vaccine in Children with Acute Leukemia," *Am. J. Dis. Children*, 1962, 103:413-418.

Mota, "Infantile Hodgkin's Disease: Remission after Measles," *Br. Med. J.*, 1973, 2:421.
Mullins and Mullins, "Molecular Medicine in Genetically Engineered Animals. Transgenesis in the Rat and Larger Mammals," *J. Clin. Invest.*, 1996, 97(7):1557-1560.
Murakami and Etlinger, "Degradation of Proteins with Blocked Amino Groups by Cytoplasmic Proteases," *Biochem. Biomes. Res. Comm.*, 1987, 146(3):1249-1255.
Nagasawa et al., "Changes of plasma levels of human growth hormone with age in relation to mammary tumour appearance in whey acidic protein/human growth hormone (mWAP/hGH) transgenic female and male mice," *In Vivo*, 1996, 10(5):503-505.
Neagoe and Stolan, "Methods of Active Immunotherapy and Viral Oncolysis in some Forms of Cancer," *Rev. Roum. Med.-Med. Int.*, 1986, 24(2):125-142.
Nemunaitis, "Oncolytic viruses,"*Investigational New Drugs*, 1999, 17:375-386.
Ohara et al., "Molecular Cloning and Sequence Determination of DA Strain of Theiler's Murine Encephalomyelitis Viruses," *Virology*, 1988, 164:245-255.
Okamoto et al., "Full-Length Sequence of a Hepatitis C Virus Genome Having Poor Homology to Reported Isolates: Comparative Study of Four Distinct Genotypes," *Virology*, 1992, 188:331-341.
Okuno et al., "Studies on the Use of Mumps Virus for Treatment of Human Cancer," *Biken J.*, 1978, 212:37-49.
Ott et al., "Measurement of radiation dose to the thyroid using positron emission tomography," *Br. J. Radiol.*, 1987, 60:245-251.
Paillard, "Bystander Effects in Enzyme/Prodrug Gene Therapy," 1997, 8:1733-1736 *Human Gene Ther.*, 8:1733-1736.
Palmenberg et al., "The nucleotide and deduced amino acid sequences of the encephalomyocarditis viral polyprotein coding region," *Nucl. Acids. Res.*, 1984,12(6):2969-2985.
Parker et al., "Cancer Statistics, 1997," *CA Cancer J. Clin.*, 1997, 47:5-27.
Pasquinucci, "Possible Effect of Measles on Leukemia," *Lancet*, 1971, 7690:136.
Patel, H., "Peptide Drug Delivery," 629th Meeting—Held at the Royal Free Hospital of Medical Dec. 19-21, 1988, pp. 931-934.
Paul et al., "The entire nucleotide sequence of the genome of hepatitis A virus (isolate MBB)," *Virus Res.*, 1987, 8:153-171.
Pentlow et al., "Quantitative imaging of I-124 using positron emission tomography with applications to radioimmunodiagnosis and radioimmunotherapy," *Med. Phys.*, 1991, 18(3):357-366.
Pentlow et al., "Quantitative Imaging of Iodine-124 with PET," *J. Nucl. Med.*, 1996, 37:1557-1562.
Pevear et al., "Analysis of the Complete Nucleotide Sequence of the Picornavirus Theiler's Murine Encephalomyelitis Virus Indicates That It Is Closely Related to Cardioviruses," *J. Virol.*, 1987, 61(5):1507-1516.
Philippou et al., "An ELISA for factor X activation peptide: application to the investigation of thrombogenesis in cardiopulmonary bypass," *Br. J. Haematol.* 1995, 90:432-437.
Polonsky et al., "Use of Biosynthetic Human C-peptide in the Measurement of Insulin Secretion Rates in Normal Volunteers and Type I Diabetic Patients," *J. Clin. Invest.*, 1986, 77:98-105.
Racaniello and Baltimore, "Molecular cloning of poliovirus cDNA and determination of the complete nucleotide sequence of the viral genome," *Proc. Natl. Acad. Sci. USA*, 1981,78(8):4887-4891.
Radecke et al., "Rescue of measles viruses from cloned DNA," *Embo J.*, 1995, 14(23):5773-5784.
Reichard et al., "Newcastle Disease Virus Selectively Kils Human Tumor Cells," *J. Surg. Res.*, 1992, 52:448-453
Robbins, "Stimulation of Measles Virus Replication by Cyclic Guanosine Monophosphate," *Intervirology*, 1991, 32:204-208.
Robbins and Rapp, "Inhibition of Measles Virus Replication by Cyclic AMP," *Virology*, 1980, 106:317-326.
Rosenthal et al., "Paracrine stimulation of keratinocytes in vitro and continuous delivery of epidermal growth factor to wounds in vivo by genetically modified fibroblasts transfected with a novel chimeric construct," *in Vivo*, 1997, 11(3):201-208.
Rubin et al., "High-Resolution Positron Emission Tomography of Human Ovarian Cancer in Nude Rats Using $^{124}$I-Labeled Monoclonal Antibodies," *Gyn. Oncol.*, 1993, 48:61-67.
Russell et al., "Use of Fusogenic Membrane Glycoproteins as Novel Therapeutic Transgenes in Gliomas," *Proc. Am. Assoc. Cancer Res.*, 2000, 41:259, Abstract #1648.
Ryan et al., "The complete nucleotide sequence of enterovirus type 70: relationships with other members of the Picornaviridae," *J. Gen. Virol.*, 1990, 71:2291-2299.
Sato et al., "Attenuated mumps virus therapy of carcinoma of the maxillary sinus," *Int. J. Oral Surg.*, 1979, 8:205-211.
Schattner, "Therapeutic Role of Measles Vaccine in Hodgkin's Disease," *Lancet*, 1984, 8367:171.
Schattner et al., "Persistent Viral Infection Affects Tumorigenicity of a Neuroblastoma Cell Line," *Cell Immunol.*, 1985, 90:103-114.
Schirrmacher et al., "Immunization With Virus-Modified Tumor Cells," *Sem. Oncol.*, 1998, 25(6):677-696.
Schirrmacher et al., "Human tumor cell modification by virus infection: an efficient and safe way to produce cancer vaccine with pleiotropic immune stimulatory properties when using Newcastle disease virus," *Gene Therapy*, 1999, 6:63-73.
Schumacher et al., "Comparative analysis of IRES efficiency of dicistronic expression vectorsw in primary cells and permanent cell lines," *Anim. Cell. Tech.*, 1999, pp. 67-69.
Segni and Curro, "Tolerability of the trivalent vaccine "Triviraten berna" in atopical children and those with a history of febrile convulsions," *Giornale di Malattie Infettive e Parassitaric*, 1992, 44(11):839-846 (Summary is in English).
Shoham et al., "Augmentation of Tumor Cell Immunogenicity by Viruses—An Approach to Specific Immunotherapy of Cancer," *Nat. Immun. Cell Growth Regul.*, 1990, 9:165-172.
Sinkovics, "Oncogenes—Antioncogenes and Virus Therapy of Cancer," *Anticancer Res.*, 1989, 9:1281-1290.
Sinkovics, "Viral Oncolysates as Human Tumor Vaccines," *Intern. Rev. Immunol.*, 1991, 7:259-287.
Sinkovics and Horvath, "Can Virus Therapy of Human Cancer Be Improved by Apoptosis Induction," *Medical Hypotheses*, 1995, 44:359-368.
Sinkovics and Horvath, "Newcastle disease virus (NDV): brief history of its oncolytic strains," *J. Clin. Virol.*, 2000, 16:1-15.
Skern et al., "Human rhinovirus 2: complete nucleotide sequence and proteolytic processing signals in the capsid protein region," *Nucl. Acids. Res.*, 1985, 13(6):2111-2126.
Smanik et al., "Cloning of the Human Sodium Iodide Symporter," *Biochem. Biophys. Res. Comm.*, 1996, 226:339-345.
Smanik et al., "Expression, Exon-Intron Organization, and Chromosome Mapping of the Human Sodium Iodide Symporter," *Endocrinology*, 1997, 138(8):3555-3558.
Smith et al., "Studies on the Use of Viruses in the Treatment of Carcinoma of the Cervix," *Cancer*, 1956, 9(6):1211-1218.
Weibel et al., "Combined live measles-mumps virus vaccine," *Archives of Disease in Childhood*, 1973, 48:532-536.
Weidmann, A. et al., Proteolytic cleavage of the fusion protein but not membrane fusion is required for measles virus-induced immunosuppression in vitro. *J. Virol.*, 2000, 74(4):1985-1993.
Zygiert, "Hodgkin's Disease: Remissions after Measles," *Lancet*, 1971, 7699:593.

* cited by examiner

SEQ ID NO: 1

ATGGAGGCCGTGGAGACCGGGGAACGGCCCACCTTCGGAGCCTGGGACTACGGGGT
CTTTGCCCTCATGCTCCTGGTGTCCACTGGCATCGGGCTGTGGGTCGGGCTGGCTCG
GGGCGGGCAGCGCAGCGCTGAGGACTTCTTCACCGGGGGCCGGCGCCTGGCGGCCC
TGCCCGTGGGCCTGTCGCTGTCTGCCAGCTTCATGTCGGCCGTGCAGGTGCTGGGCG
TGCCGTCGGAGGCCTATCGCTATGGCCTCAAGTTCCTCTGGATGTGCCTGGGCCAGC
TTCTGAACTCGGTCCTCACCGCCCTGCTCTTCATGCCCGTCTTCTACCGCCTGGGCCT
CACCAGCACCTACGAGTACCTGGAGATGCGCTTCAGCCGCGCAGTGCGGCTCTGCG
GGACTTTGCAGTACATTGTAGCCACGATGCTGTACACCGGCATCGTAATCTACGCAC
CGGCCCTCATCCTGAACCAAGTGACCGGGCTGGACATCTGGGCGTCGCTCCTGTCCA
CCGGAATTATCTGCACCTTCTACACGGCTGTGGGCGGCATGAAGGCTGTGGTCTGGA
CTGATGTGTTCCAGGTCGTGGTGATGCTAAGTGGCTTCTGGGTTGTCCTGGCACGCG
GTGTCATGCTTGTGGGCGGGCCCCGCCAGGTGCTCACGCTGGCCCAGAACCACTCCC
GGATCAACCTCATGGACTTTAACCCTGACCCGAGGAGCCGCTATACATTCTGGACTT
TTGTGGTGGGTGGCACGTTGGTGTGGCTCTCCATGTATGGCGTGAACCAGGCGCAGG
TGCAGCGCTACGTGGCTTGCCGCACAGAGAAGCAGGCCAAGCTGGCCCTGCTCATC
AACCAGGTCGGCCTGTTCCTGATCGTGTCCAGCGCTGCCTGCTGTGGCATCGTCATG
TTTGTGTTCTACACTGACTGCGACCCTCTCCTCCTGGGGCGCATCTCTGCCCCAGACC
AGTACATGCCTCTGCTGGTGCTGGACATCTTCGAAGATCTGCCTGGAGTCCCCGGGC
TTTTCCTGGCCTGTGCTTACAGTGGCACCCTCAGCACAGCATCCACCAGCATCAATG
CTATGGCTGCAGTCACTGTAGAAGACCTCATCAAACCTCGGCTGCGGAGCCTGGCAC
CCAGGAAACTCGTGATTATCTCCAAGGGGCTCTCACTCATCTACGGATCGGCCTGTC
TCACCGTGGCAGCCCTGTCCTCACTGCTCGGAGGAGGTGTCCTTCAGGGCTCCTTCA
CCGTCATGGGAGTCATCAGCGGCCCCCTGCTGGGAGCCTTCATCTTGGGAATGTTCC
TGCCGGCCTGCAACACACCGGGCGTCCTCGCGGGACTAGGCGCGGGCTTGGCGCTG
TCGCTGTGGGTGGCCTTGGGCGCCACGCTGTACCCACCCAGCGAGCAGACCATGAG
GGTCCTGCCATCGTCGGCTGCCCGCTGCGTGGCTCTCTCAGTCAACGCCTCTGGCCT
CCTGGACCCGGCTCTCCTCCCTGCTAACGACTCCAGCAGGGCCCCCAGCTCAGGAAT
GGACGCCAGCCGACCCGCCTTAGCTGACAGCTTCTATGCCATCTCCTATCTCTATTA
CGGTGCCCTGGGCACGCTGACCACTGTGCTGTGCGGAGCCCTCATCAGCTGCCTGAC
AGGCCCCACCAAGCGCAGCACCCTGGCCCCGGGATTGTTGTGGTGGGACCTCGCAC
GGCAGACAGCATCAGTGGCCCCCAAGGAAGAAGTGGCCATCCTGGATGACAACTTG
GTCAAGGGTCCTGAAGAACTCCCCACTGGAAACAAGAAGCCCCCTGGCTTCCTGCC
CACCAATGAGGATCGTCTGTTTTTCTTGGGGCAGAAGGAGCTGGAGGGGCTGGCTC
TTGGACCCCCTGTGTTGGACATGATGGTGGTCGAGACCAGCAGGAGACAAACCTCT
GA

*Fig. 1*

SEQ ID NO: 2

MEAVETGERPTFGAWDYGVFALMLLVSTGIGLWVGLARGGQRSAEDFFTGGRRLAALP
VGLSLSASFMSAVQVLGVPSEAYRYGLKFLWMCLGQLLNSVLTALLFMPVFYRLGLTS
TYEYLEMRFSRAVRLCGTLQYIVATMLYTGIVIYAPALILNQVTGLDIWASLLSTGIICTF
YTAVGGMKAVVWTDVFQVVVMLSGFWVVLARGVMLVGGPRQVLTLAQNHSRINLM
DFNPDPRSRYTFWTFVVGGTLVWLSMYGVNQAQVQRYVACRTEKQAKLALLINQVGL
FLIVSSAACCGIVMFVFYTDCDPLLLGRISAPDQYMPLLVLDIFEDLPGVPGLFLACAYSG
TLSTASTSINAMAAVTVEDLIKPRLRSLAPRKLVIISKGLSLIYGSACLTVAALSSLLGGG
VLQGSFTVMGVISGPLLGAFILGMFLPACNTPGVLAGLGAGLALSLWVALGATLYPPSE
QTMRVLPSSAARCVALSVNASGLLDPALLPANDSSRAPSSGMDASRPALADSFYAISYL
YYGALGTLTTVLCGALISCLTGPTKRSTLAPGLLWWDLARQTASVAPKEEVAILDDNLV
KGPEELPTGNKKPPGFLPTNEDRLFFLGQKELEGAGSWTPCVGHDGGRDQQETNL

*Fig. 2*

SEQ ID NO: 3

ATGGAGGGTGCGGAGGCCGGGGCCCGGGCCACCTTCGGCGCCTGGGACTACGGCGT
GTTCGCGACCATGCTGCTGGTGTCCACGGGCATCGGGCTATGGGTCGGCCTGGCCCG
CGGTGGCCAACGCAGTGCCGACGACTTCTTTACCGGGGGCCGGCAGTTGGCAGCCG
TTCCTGTGGGGCTGTCGCTGGCCGCCAGTTTCATGTCGGCTGTGCAGGTGCTCGGGG
TCCCCGCCGAGGCAGCGCGCTACGGGCTCAAGTTCCTGTGGATGTGCGCGGGTCAGT
TGCTCAACTCGCTGCTCACAGCGTTTCTCTTCTTGCCGATCTTCTACCGCCTGGGCCT
TACCAGCACCTACCAGTACCTAGAGCTGCGCTTCAGCCGAGCGGTCCGGCTCTGCGG
GACGCTGCAGTACTTGGTGGCCACGATGCTGTATACAGGCATCGTGATCTACGCGCC
TGCGCTCATCCTGAACCAAGTGACCGGGTTGGACATCTGGGCATCGCTCCTGTCCAC
AGGAATCATCTGCACCTTGTACACTACCGTGGGTGGTATGAAGGCCGTGGTCTGGAC
AGATGTGTTCCAGGTTGTGGTAATGCTCGTTGGCTTCTGGGTGATCCTGGCCCGAGG
CGTCATTCTCCTGGGGGGTCCCCGGAACGTGCTCAGCCTCGCTCAGAACCATTCCCG
GATCAACCTGATGGACTTTGACCCTGATCCTCGGAGCCGGTACACCTTCTGGACTTT
CATAGTGGGTGGCACACTGGTGTGGCTCTCCATGTACGGTGTGAACCAAGCCCAGGT
ACAGCGCTATGTGGCCTGCCACACAGAGGGAAAGGCCAAACTGGCCCTGCTTGTCA
ACCAGCTGGGCCTCTTCCTGATTGTGGCCAGTGCAGCTTGCTGTGGCATTGTCATGTT
CGTCTACTACAAGGACTGTGACCCCCTCCTCACAGGCCGTATCTCAGCCCCCGACCA
GTACATGCCGCTGCTTGTGTTGGACATTTTTGAGGATCTGCCCGGGGTCCCCGGGCT
CTTCCTGGCCTGTGCCTACAGTGGCACCCTCAGCACTGCATCCACCAGCATCAACGC
CATGGCAGCTGTGACTGTGGAAGACCTCATCAAGCCGAGGATGCCTGGCCTGGCAC
CTCGGAAGTTGGTTTTCATCTCTAAAGGGCTCTCATTCATCTACGGCTCTGCCTGCCT
CACTGTGGCTGCTCTGTCCTCACTGCTGGGAGGTGGTGTCCTCCAGGGTTCCTTCACT
GTGATGGGTGTCATCAGTGGGCCTCTACTAGGCGCCTTCACGCTTGGGATGCTGCTC
CCAGCCTGCAACACGCCAGGCGTTCTCTCCGGGTTGGCAGCAGGCTTGGCTGTATCC
CTGTGGGTGGCCGTAGGGGCCACACTGTATCCCCCTGGAGAGCAGACCATGGGGGT
GCTGCCCACCTCGGCTGCAGGCTGCACCAACGATTCGGTCCTCCTGGGCCCACCTGG
AGCCACCAACGCTTCCAACGGGATCCCCAGTTCTGGAATGGACACGGGCCGCCCTG
CCCTCGCTGATACCTTTTACGCCATCTCCTATCTCTATTACGGGGCTCTGGGCACGCT
GACCACCATGCTTTGCGGTGCTCTCATCAGCTACCTTACTGGTCCCACCAAGCGCAG
CTCCCTGGGTCCCGGATTGCTGTGGTGGGACCTTGCTCGACAGACAGCGTCTGTGGC
CCCAAAGGAAGACACTGCCACCCTGGAGGAGAGCCTGGTGAAGGGACCGGAAGAC
ATCCCTGCTGTGACCAAGAAGCCCCCTGGCCTCAAGCCAGGCGCCGAGACCCACCC
CCTGTATCTGGGGCACGATGTGGAGACCAACCTCTGA

*Fig. 3*

SEQ ID NO: 4

MEGAEAGARATFGAWDYGVFATMLLVSTGIGLWVGLARGGQRSADDFFTGGRQLAA
VPVGLSLAASFMSAVQVLGVPAEAARYGLKFLWMCAGQLLNSLLTAFLFLPIFYRLGLT
STYQYLELRFSRAVRLCGTLQYLVATMLYTGIVIYAPALILNQVTGLDIWASLLSTGIICT
LYTTVGGMKAVVWTDVFQVVVMLVGFWVILARGVILLGGPRNVLSLAQNHSRINLMD
FDPDPRSRYTFWTFIVGGTLVWLSMYGVNQAQVQRYVACHTEGKAKLALLVNQLGLF
LIVASAACCGIVMFVYYKDCDPLLTGRISAPDQYMPLLVLDIFEDLPGVPGLFLACAYSG
TLSTASTSINAMAAVTVEDLIKPRMPGLAPRKLVFISKGLSFIYGSACLTVAALSSLLGGG
VLQGSFTVMGVISGPLLGAFTLGMLLPACNTPGVLSGLAAGLAVSLWVAVGATLYPPG
EQTMGVLPTSAAGCTNDSVLLGPPGATNASNGIPSSGMDTGRPALADTFYAISYLYYGA
LGTLTTMLCGALISYLTGPTKRSSLGPGLLWWDLARQTASVAPKEDTATLEESLVKGPE
DIPAVTKKPPGLKPGAETHPLYLGHDVETNL

*Fig. 4*

Fig. 10
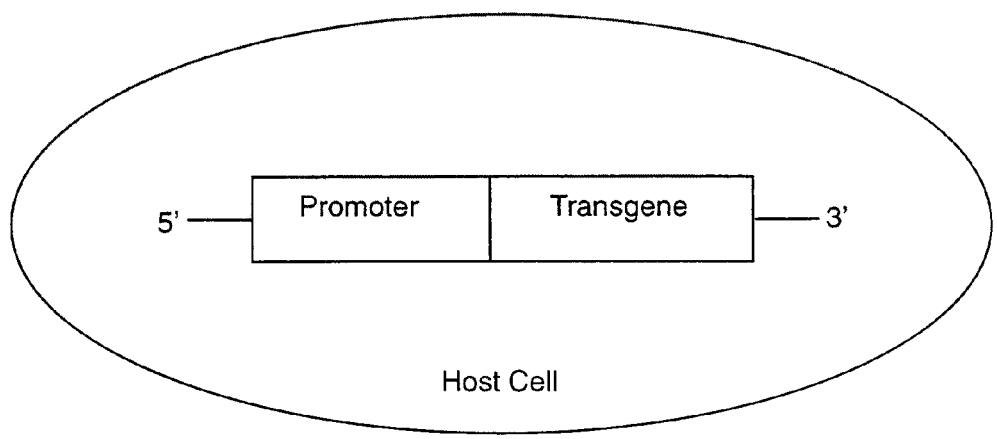
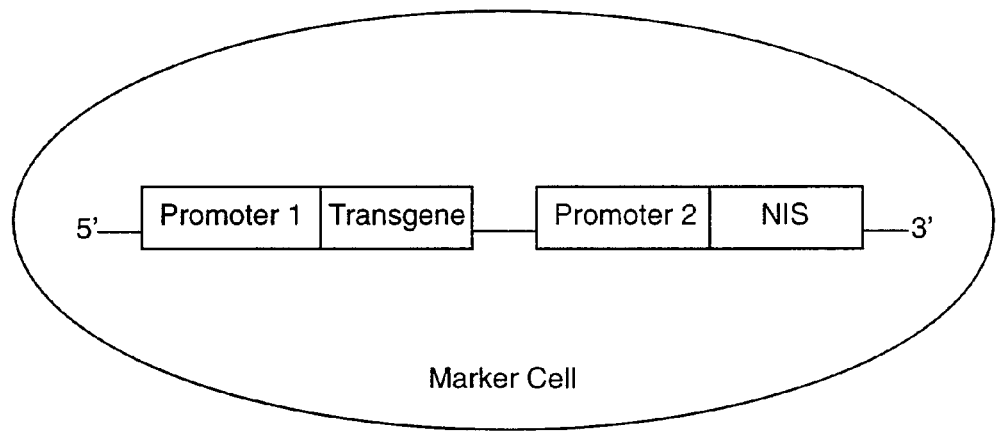

Fig. 11
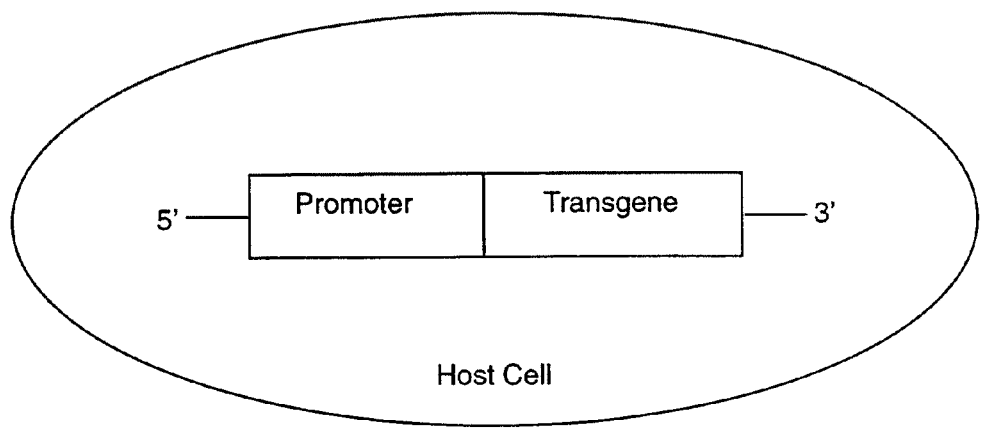
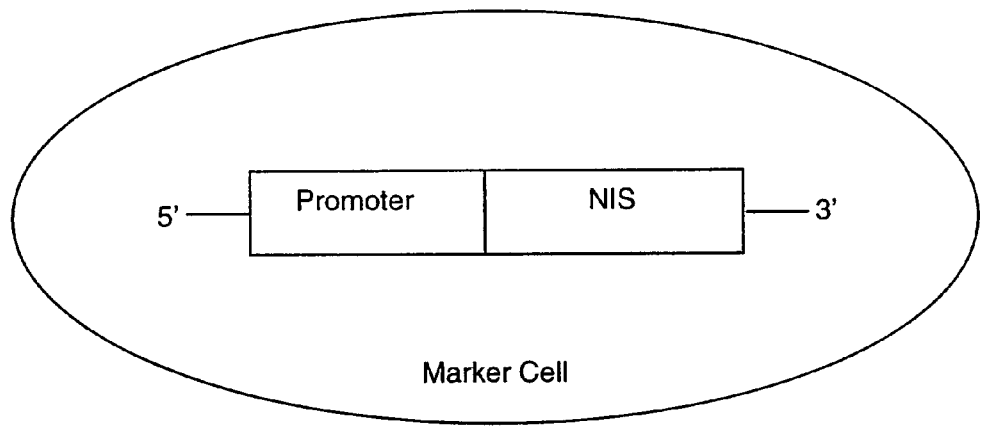

SYSTEM FOR MONITORING THE LOCATION OF TRANSGENES

CROSS-REFERENCE TO RELATED APPLICATION

This application as a divisional of U.S. application Ser. No. 10/428,868, filed May 1, 2003, which is a continuation of U.S. application Ser. No. 09/640,198 (now U.S. Pat No. 6,586,411, ) filed Aug. 16, 2000. The disclosures of the prior applications are considered part of (and are incorporated by reference in) the disclosure of this application.

BACKGROUND OF THE INVENTION

In the context of gene therapy in a mammal, it is important to monitor the localization of a transgene. Where the transgene encodes a therapeutic polypeptide, such as a protein targeted to kill cancer cells, it is advantageous to have information as to the location, that is, the specific organs, tissues and/or cells which are expressing the polypeptide. There is a need in the art for methods and materials that permit the monitoring of tissue- or cell-specific transgene expression without the requirement to sample and directly test genetically modified cells or tissues.

SUMMARY OF THE INVENTION

The invention contemplates a method of monitoring the location of a transgene in a mammal, comprising the steps of (a) administering to a mammal in need thereof nucleic acid comprising a transgene and a sequence encoding a sodium-iodide symporter (NIS), wherein expression of NIS in cells permits cellular uptake of iodine (b) administering to a mammal labeled iodine in an amount sufficient to permit transport of the labeled iodine by MS and detection of transported labeled iodine; and (c) detecting the location of the transported labeled iodine in the mammal as an indication of the location of the transgene.

In some embodiments, the step of detecting is performed quantitatively to determine the amount of transported labeled iodine in a mammal. The location of the transported labeled iodine is indicative of the location of NIS, whereby the location of NIS is indicative of the location of the transgene.

The invention also provides a method of monitoring the location of a transgene in a mammal, comprising the steps of (a) transfecting a host cell ex vivo with nucleic acid comprising a transgene and a sequence encoding and expressing NIS, wherein the MS permits cellular uptake of iodine by the host cells; (b) introducing the transfected host cell into a mammal; (c) administering to the mammal labeled iodine in an amount sufficient to permit transport of the labeled iodine by MS and detection of transported labeled iodine; and (d) determining the location of transported labeled iodine in the mammal; whereby the location of transported labeled iodine is indicative of the location of the transgene.

In preferred embodiments, the labeled iodine is radioactive iodine.

The invention also provides a nucleic acid construct comprising a chimeric gene comprising the transgene and the sequence encoding an NIS, wherein the chimeric gene also comprises a sequence encoding a protease-cleavable linker between the transgene and the sequence encoding NIS.

In a further embodiment, the sequence encoding the protease-cleavable amino acid linker comprises a sequence encoding an auto-cleaving sequence.

The invention also provides a nucleic acid construct comprising a first promoter operably associated with the transgene and a second promoter operably associated with the sequence encoding MS.

The invention further provides a nucleic acid construct comprising a chimeric gene comprising a transgene and the sequence encoding NIS, wherein the chimeric gene also comprises between the transgene and the sequence encoding MS, a sequence encoding an internal ribosome entry site.

In a preferred embodiment, the sequence encoding a protease cleavable linker is attached to the 5' end of the transgene.

In another preferred embodiment, the sequence encoding the protease-cleavable linker is attached to the 3' end of the transgene.

In a preferred series of embodiments, the protease cleavable linker is cleaved by furin, or is identical to a linker present in a cytoplasmic protein.

In another series of preferred embodiments, the transgene encodes a fusogenic polypeptide, the fusogenic polypeptide encodes a viral fusion protein, the fusogenic polypeptide encodes a measles virus H glycoprotein, or the fusogenic polypeptide encodes a gibbon ape leukemia virus envelope glycoprotein.

The invention additionally provides a host cell comprising (a) a nucleic acid construct comprising a sequence encoding a transgene and a sequence encoding a sodium-iodide symporter (NIS), wherein the chimeric gene also comprises a sequence encoding a protease-cleavable linker between the transgene and the sequence encoding NIS; (b) a construct comprising a first promoter operable associated with the transgene and a second promoter is operable associated with the sequence encoding NIS; or (c) a construct comprising a chimeric gene comprising the transgene and the sequence encoding NIS, wherein the chimeric gene also comprises between the transgene and the sequence encoding NIS, a sequence encoding an internal ribosome entry site.

The invention further provides a kit comprising, in a ready to use format, one or more of the nucleic acid constructs described above, and one or more reagents for monitoring the location of the transported labeled iodine.

The invention still further provides a kit comprising, in a ready to use format, a host cell transfected with one or more of the nucleic acid constructs described above, and one or more reagents for monitoring the location of the transported labeled iodine.

In a preferred embodiment, the reagents of the kit include labeled iodine.

In a preferred embodiment, the reagents of the kit include radioactive iodine.

The invention thus provides the art with methods and materials for conveniently and effectively monitoring the tissue-specific distribution of expressed transgenes in cells, tissues, animals or human patients without the need for disruptive sampling methods including surgery.

As used herein, "cell-associated protease" refers to any protease within the cell, such as a protease located in the cytoplasm, or within, or associated with an organelle. As used herein, "cell-associated protease" also refers to any protease associated with the cell, including, but not limited to a protease located on the cell surface or in the extracellular space near the cell surface, such that the protease cleaves a peptide with the appropriate sequence near the cell surface.

As used herein, "mammal" refers to any warm blooded organism of the class Mammalia, including, but not limited to rodents, feline, canine, or ungulates. In preferred embodiments of the invention, a "mammal" is a human.

As used herein, "transgene" refers to any nucleic acid sequence introduced into a cell and which encodes a polypeptide of interest. As used herein a "transgene" can be a gene which is endogenous to the mammal of the present invention, and which may or may not be endogenously expressed by the cells of the invention into which it is introduced. According to the present invention, a "transgene" can be applied to remedy a disease condition in the process known as gene therapy.

As used herein, "auto-cleaving sequence" refers to a short polypeptide sequence of between 10 and 20 amino acids, but preferably between 12 and 18 amino acids, but more preferably between 15 and 17 amino acids, in which cleavage of the propeptide at the C-terminus occurs cotranslationally in the absence of a cell associated protease. Moreover, cleavage can occur in the presence of heterologous sequence information at the 5' and/or 3' ends of the "auto-cleaving sequence". An example of an "auto-cleaving sequence" useful in the present invention is the that of the foot and mouth disease virus (FMDV) 2A propeptide, in which cleavage occurs at the C-terminus of the peptide at the final glycine-proline amino acid pair. Cleavage of FMDV 2A propeptide is independent of the presence of other FMDV sequences and can generate cleavage in the presence of heterologous sequences. Insertion of this sequence between two protein coding regions results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (P. deFelipe et al., Gene Therapy 6: 198-208 (1999)). Thus, instead of using a cleavage signal recognizable by a cell-associated protease, the self-cleaving FMDV 2A protease sequence can be employed to link the NIS to the polypeptide encoded by the transgene, resulting in spontaneous release of the NIS from the polypeptide encoded by the transgene.

As used herein, a "fusogenic polypeptide" refers to a membrane glycoprotein, including, but not limited to Type I and Type II membrane glycoproteins, which kill cells on which they are expressed by fusing the cells into a partial or complete multinucleated syncytia, which die by sequestration of cell nuclei and subsequent nuclear fusion. Examples of "fusogenic polypeptides" include, but are not limited to gibbon ape leukemia virus and measles virus H glycoprotein.

As used herein, "detecting" refers to the use any in vivo, ex vivo, or in vitro imaging technique capable of measuring a radio-labeled moiety, including, but not limited to standard single positron emission computed tomography (SPECT) or positron emission tomography (PET) imaging systems, used to measure the amount of labeled iodine in a mammal. Labeled iodine of the present invention is "detected" if the levels of labeled iodine measured following administration of one or more of the nucleic acid constructs described above, or the host cells transfected with one or more of the nucleic acid constructs described above are at all higher than the levels measured prior to administration. Labeled iodine of the present invention is also "detected" if it is localized to one or more organs, tissues, or cells following the administration of one or more of the nucleic acid constructs described above, or the host cells transfected with one or more of the nucleic acid constructs described above, that it was not localized to prior to the administration of the constructs or cells. According to the invention, labeled iodine is "detected" if the quantitative or semi-quantitative measurements of labeled iodine yield levels which are between 0.001-90% of the administered labeled iodine dose, preferably between 0.01-70%, preferably between 0.1-50%, more preferably between 1.0-20%, more preferably between 5-10% of the administered labeled iodine dose. In a preferred embodiment, the concentration of labeled iodine in organs, tissues, or cells can be determined by comparing the quantity of labeled iodine measured by methods of the invention, including, but not limited to SPECT or PET, to a standard sample of known labeled iodine concentration.

As used herein, "transported" refers to the movement of labeled iodine from the outside of one or more cells to the inside of one or more cells as a result of the expression of an NIS by the cell or cells which "transported" the labeled iodine. Labeled iodine is considered to be "transported" if the measured levels of iodine in organs, tissues or cells of the invention are between 0.001-90% of the administered labeled iodine dose, preferably between 0.01-70%, preferably between 0.1-50%, more preferably between 1.0-20%, more preferably between 5-10% of the administered labeled iodine dose.

As used herein, the biological activity of an NIS polypeptide, referred to herein as "NIS activity" or "NIS function" is the transport or sequestration of iodine across the cell membrane, i.e., from outside a cell to inside a cell. NIS is an intrinsic membrane glycoprotein with 13 putative transmembrane domains which is responsible for the ability of cells of the thyroid gland to transport and sequester iodide. AN NIS polypeptide useful in the invention with "NIS activity" or "NIS function" thus is a membrane glycoprotein with a transmembrane domain and is capable of transporting iodine if the polypeptide is present in a thyroid cell, and can also transport iodine in a non-thyroid cell type described herein.

As used herein, "a sequence encoding an NIS", or an "NIS gene" refers to a nucleotide sequence encoding a polypeptide having the activity of a sodium iodide symporter (NIS). Examples of NIS nucleotide sequences and amino acid sequences include, but are not limited to, SEQ ID Nos 1 and 3 and SEQ ID Nos 2 and 4 respectively, as shown in FIGS. 1-4. NIS nucleotide and/or amino acid sequences also include, but are not limited to homologs or analogs of the nucleotide and/or amino acid sequences of FIGS. 1-4, wherein "homologs" are natural variants of NIS which retain NIS activity, and "analogs" are engineered variants of NIS which retain NIS activity.

An advantage of the present invention is that the transgene location can be monitored with out adversely affecting the mammal or the cell. That is, NIS is a self-protein, and as such does not stimulate a host immune reaction. Furthermore, the NIS functions solely to sequester iodine into a cell, which does not adversely affect normal cellular function, or overall cell biology.

Further features and advantages of the invention will become more fully apparent in the following description of the embodiments and drawings thereof, and from the claims

BRIEF DESCRIPTION OF THE DRAWINGS

FIG. 1 displays the nucleotide sequence of SEQ ID NO: 1 which encodes human NIS.

FIG. 2 displays the amino acid sequence of human NIS (SEQ ID NO: 2).

FIG. 3 displays the nucleotide sequence of SEQ ID NO: 3 which encodes rat NIS.

FIG. 4 displays the amino acid sequence of rat NIS (SEQ ID NO: 4)

FIG. 10 displays a mixed host cell population comprising one or more cells which contain a nucleic acid construct comprising a first promoter operably linked to a transgene and a second promoter operably linked to a sequence encoding NIS (marker cells), and one or more cells which contain a nucleic acid construct comprising a transgene alone.

FIG. 11 displays a mixed host cell population comprising one or more cells which contain a nucleic acid construct comprising a sequence encoding NIS (marker cells), and one or more cells which contain a nucleic acid construct comprising a transgene.

DETAILED DESCRIPTION

Figure 5:
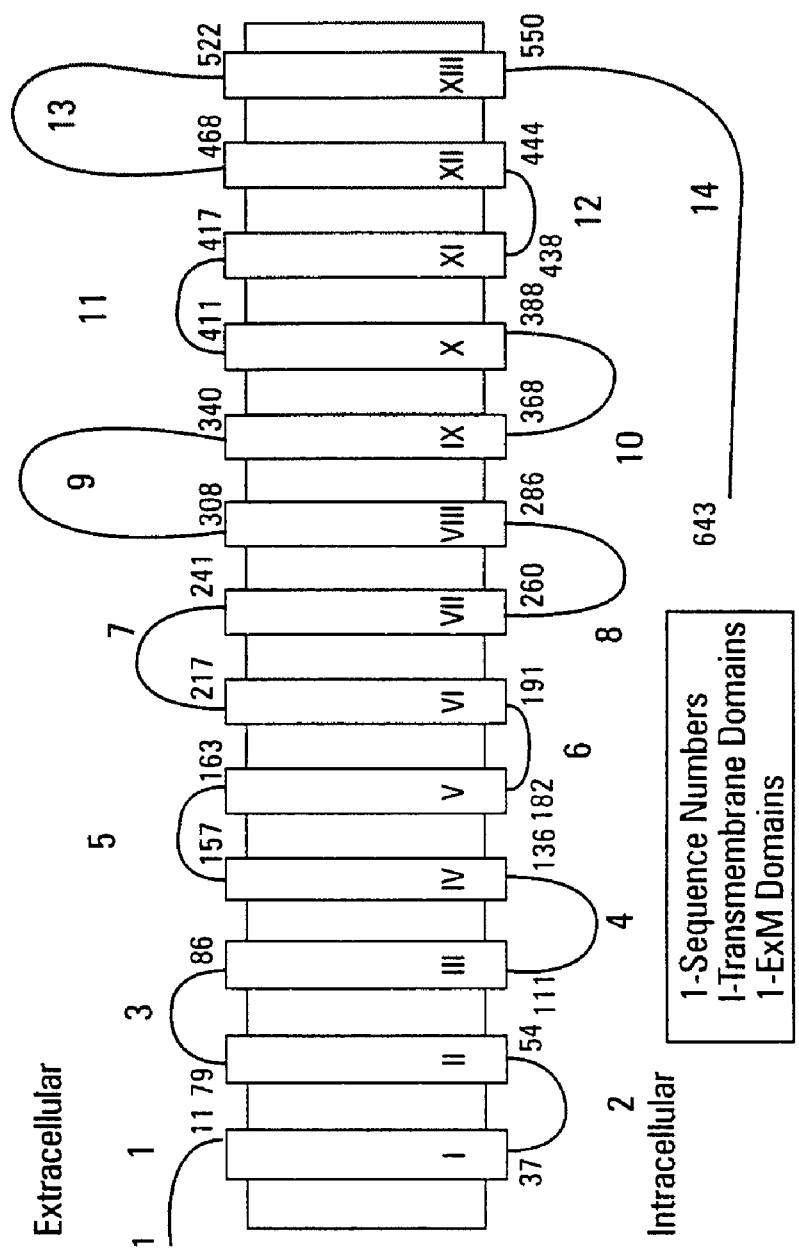
FIG. 5 displays a schematic representation of the sodium-iodide symporter in the cell membrane.

The present invention provides a novel method of monitoring the distribution in a cell or tissue of a transgene in vivo. The present invention encompasses localizing the presence and/or expression of a transgene comprising administering to a mammal a nucleic acid comprising (a) a chimeric nucleic acid sequence encoding the transgene and a sequence encoding the NIS, wherein the chimeric construct also comprises a sequence encoding a protease-cleavable linker between the transgene and the sequence encoding the NIS, (b) a nucleic acid sequence wherein a first promoter is operably associated with the transgene and a second promoter is operably associated with the sequence encoding the NIS, or (c) a chimeric gene comprising the transgene and the sequence encoding the NIS, wherein the chimeric gene also comprises, between the transgene and the sequence encoding the NIS, a sequence encoding an internal ribosome entry site; or administering to a mammal a cell transfected with a nucleic acid construct of one or more of (a), (b), or (c) as described above.

According to an embodiment of the invention a NIS is genetically fused to the N-terminus or the C-terminus of the polypeptide product of a transgene such that the activities of both polypeptides are present in the polypeptide. According to a preferred embodiment of the invention, the NIS and the polypeptide product of the transgene are associated through a linker polypeptide that is cleavable by a cell-associated protease.

The protease cleavage signal is chosen such that at some point during the subsequent folding, assembly, and transport of the molecule within a cell, a cell-associated protease cleaves the NIS from the transgene product. The mammal is subsequently administered labeled iodine, which is transported into any cell which possesses an NIS. The labeled iodine can then be localized using non-invasive imaging techniques such as SPECT or PET, such that localization of labeled iodine indicates the expression of the transgene product.

In a variation of this embodiment, the construct does not encode a protease-cleavable linker, but instead the NIS is operationally associated with a different promoter from that which is associated with the transgene. In yet another variation of this embodiment, the construct does not encode a protease-cleavable linker, but instead the construct is transcribed to a polycistronic mRNA which comprises a ribosome entry site between the transgene and the sequence encoding the NIS.

Still another embodiment of the invention provides another method for monitoring the localization of a transgene. A cell that has been transfected ex vivo with the nucleic acid construct described above (host cell) is introduced into a mammal. Expression of the transgene and NIS from the host cell will lead to the transport of labeled iodine from the outside to the inside of the host cell. The labeled iodine may be localized by standard SPECT or PET scan as an indication of the location of transgene expression. In a variation of this embodiment, the cell is transfected with a construct that does not encode a protease-cleavable linker. Instead, the NIS is operationally associated with a different promoter from that which is associated with the transgene. In another variation of this embodiment, the cell is transfected with a construct that is transcribed to a polycistronic mRNA which comprises an internal ribosome entry site between the transgene and the sequence encoding the NIS. Because of the position of the ribosome entry site, both the transgene product and the NIS are expressed separately without the need for protease cleavage.

Yet another embodiment of the invention provides a method of monitoring the location of a therapeutic transgene. In this embodiment, the nucleic acid construct of this invention is used to transfect a cell as explained in either of the two previous embodiments. In this case, the transgene is a therapeutic gene which is introduced into a mammal to remedy a functional deficiency, treat a pathological condition, or destroy certain cells of the mammal by the activity of the transgene product. Detection of transgene localization may be used to gage the progress of therapy, and to insure that the tissue-specific distribution of the transgene is appropriate for the intended treatment. In some versions of this embodiment, a transgene product which destroys cancer cells is monitored as a means of assessing the effectiveness of the therapy and deciding whether to repeat or adjust the therapy.

The transgene of the present invention is any nucleic acid sequence introduced into a cell. Transgenes can be applied to remedy a disease condition in the process known as gene therapy. The term gene therapy can be applied to any therapeutic procedure in which genes or genetically modified cells are administered for therapeutic benefit. For some uses of the invention the transgene will be one which encodes a polypeptide that selectively kills a certain group of undesired cells such as cancer cells. For example, the transgene can encode a fusogenic polypeptide such as a viral fusion protein or an artificial polypeptide which causes the fusion of cells expressing the polypeptide, resulting in syncytium formation and cell death. The transgene can be introduced into a target cell or host cell by any mechanism of transfer known in the art, including any type of gene therapy, gene transfer, transfection, and the like.

Sodium-Iodide Symporter

Current treatments for thyroid cancers utilize radioactive iodine therapy, given the intrinsic ability of thyroid cells, cancerous or not, to concentrate iodine from extracellular fluid. The iodine trapping activity of thyroidal cells is utilized in diagnosis as well as therapy of thyroid cancer. Functioning thyroid cancer metastases can be detected by administering radioiodine and then imaging with a gamma camera.

Recently, the mechanism mediating iodide uptake across the basloateral membrane of thyroid follicular cells has been elucidated by cloning and characterization of the sodium iodide symporter (FIG. 5; Smanik et al., *Biochem Biophys Res Commun.* 226:339-45 (1996); Dai et al., *Nature.* 379: 458-60 (1996)). NIS is an intrinsic membrane glycoprotein with 13 putative transmembrane domains which is responsible for the ability of cells of the thyroid gland to transport and sequester iodide. An NIS of the present invention is comprised of a polypeptide having the activity of a sodium iodide symporter, including, but not limited to the polypeptide encoded by the amino acid sequences of SEQ ID Nos 2 and 4 for human and rat respectively, wherein the amino acid sequences of SEQ ID Nos 2 and 4 are encoded by polynucleotide sequences comprising SEQ ID Nos 1 and 3 for human and rat respectively, or an analog thereof. NIS expression in thyroid tissues is dependent upon stimulation of the cells by pituitary-derived thyroid stimulating hormone (TSH) and can therefore be readily suppresses in this tissue by treatment with Thyroxine. TSH-regulated NIS expression is specific for thyroid cells, whereas many other organs do not concentrate iodine due to lack of NIS expression. Cloning and characterization of the human and rat NIS genes (SEQ ID NO: 1 and 3 respectively; GenBank Accession numbers A005796 and U60282 respectively) permits NIS gene delivery into non-thyroid cells, thereby allowing these cells to trap and sequester radio-labeled iodine.

According to the present invention, the NIS functions well as a localization tag for several reasons. The NIS, according to the present invention, is synthesized in the mammal, using the mammals own protein synthetic machinery, and thus is recognized as self, thereby avoiding a potential immune response. Furthermore, the NIS is a useful localization tag according to the present invention as it should have no significant effect on the biological properties of the genetically modified cells. Given that the only known function of the NIS is to transport iodine across the cell membrane, it should not adversely affect endogenous cellular function.

Nucleic Acid Constructs

Figure 6:
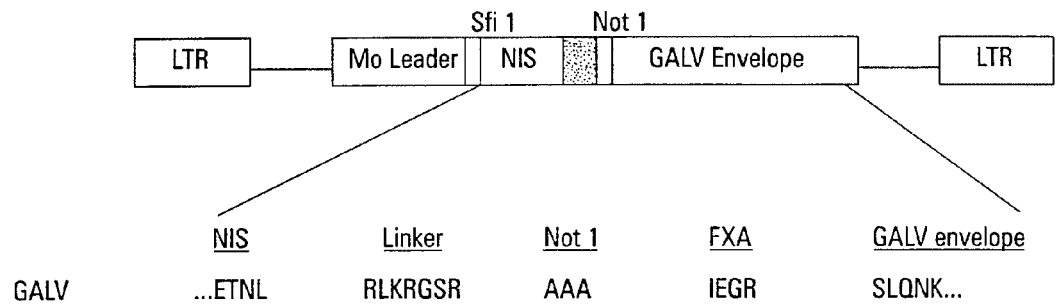
FIG. 6 displays the expression constructs of the present invention in which the sequence encoding the NIS is linked to the N-terminus of the gibbon ape leukemia virus (GALV) envelope protein via a furin cleavable linker. The expressed polypeptide includes, from N-terminal to C-terminal, NIS (represented by the last four amino acids (ETNL) of SEQ ID NOs:2 and 4), a furin cleavable linker (RLKRGSR; SEQ ID NO:27), a Not 1 site, a factor Xa cleavage site (FXA; represented by the amino acids IEGR (SEQ ID NO:28)), and GALV envelope protein (represented by the amino acids SLQNK (SEQ ID NO:29)).
Figure 7:
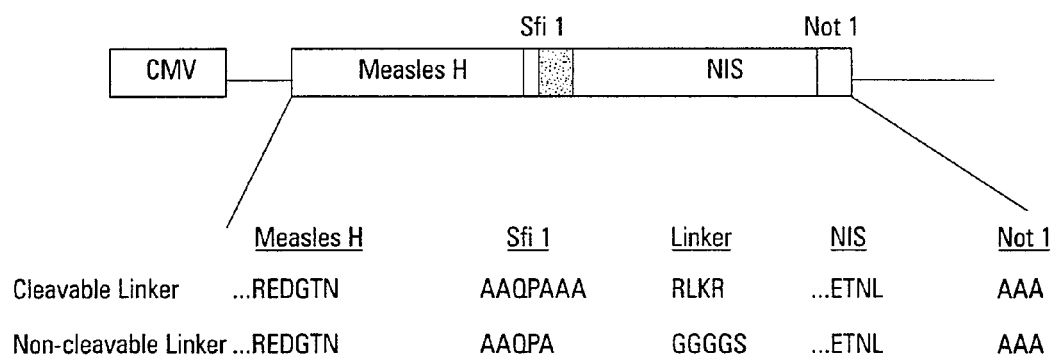
FIG. 7 displays an expression construct of the present invention in which the sequence encoding the NIS is linked to the C-terminus of measles virus H glycoprotein via a furin cleavable linker or via a non-cleavable linker. The expressed polypeptide includes, from N-terminal to C-terminal, measles virus H glycoprotein (represented by the amino acids REDGTN (SEQ ID NO:30)), an Sfi 1 site (represented by the amino acids AAQPAAA (SEQ ID NO:31) or AAQPA (SEQ ID NO:32)), a cleavable or non-cleavable linker (represented by RLKR (SEQ ID NO:33) and GGGGS (SEQ ID NO:34), respectively), NIS (represented by the last four amino acids (ETNL) of SEQ ID NOs:2 and 4), and a Not 1 site.

Central to the use of the invention is the creation and/or use of a nucleic acid construct comprising sequences encoding a transgene, a NIS, and optionally a protease-cleavable linker (FIGS. 6 and 7). The nucleic acid construct can be an expression vector, a plasmid that can be prepared and grown in bacteria, or an engineered virus capable of transfecting the host cell. The nucleic acid sequences of the construct can contain DNA, RNA, a synthetic nucleic acid, or any combination thereof, as known in the art. The nucleic acid construct can be packaged in any manner known in the art consistent with its delivery to a target cell. For example, the construct can be packaged into a liposome, a DNA- or retro-virus, or another structure. The sequences should be arranged so that the protease-cleavable linker peptide, if one is included, is situated between the transgene product and the NIS, resulting in the cleavage of the NIS from the transgene product by a selected protease, which can be a protease that is encountered in the host cell or organism during post-translational processing. One means of accomplishing this is to design the nucleic acid construct such that the sequences encoding both the NIS and the linker polypeptide are attached to either the 3' end or the 5' end of the transgene. The sequences encoding each of the three components may be interspersed with other sequences as needed. However, in order for the NIS to be cleaved from the transgene product during processing, it is necessary that the protease cleavable linker sequence be interposed between the transgene product and the NIS.

Promoters of the invention include, but are not limited to any promoter that is operable in a selected host cell according to the invention. Additionally, a promoter of the invention can be the endogenous promoter for NIS or the endogenous promoter for a transgene, or can be any promoter that will be operative in the expression of the sequence encoding the NIS, or the transgene in a host cell of the invention.

Preferably, the sequences encoding each of the three components (the transgene product, the linker, and the NIS) are all under control of a single promoter sequence, resulting in the expression of a fusion protein containing each of the three elements. This assures that the NIS and the transgene product will be synthesized in stoichiometric proportion, which is preferred because it results in similar levels and location of expression for both the transgene product and the NIS. The chosen promoter can be one which regulates the expression of the transgene in a manner consistent with its use in the host organism, for example, in a manner consistent with the intended gene therapy. The expression of the NIS can be driven from a second promoter inserted into the construct or it can be encoded on the same transcript as the transgene, but translated from an internal ribosome entry site. The use of two or more separate promoters is less likely to produce the desired stoichiometry of expression. However, the use of two promoters can, in some embodiments, obviate the need for including a protease-cleavable linker peptide. If the NIS is regulated by a separate promoter, it will be translated separately from the transgene product without requiring proteolysis. While the two promoters regulating the transgene and the NIS can be different, they can also be the same promoter, in which case the expression of both transgene and NIS are quite likely to be parallel, thereby increasing the effectiveness of the NIS for monitoring the tissue-specific distribution of the transgene.

Another alternative strategy to using a protease-cleavable linker is to include an internal ribosome entry site in the construct between the transgene and the coding sequence for the NIS. Internal ribosomal entry sites (IRES, also called ribosomal landing pads) are sequences that enable a ribosome to attach to mRNA downstream from the 5' cap region and scan for a downstream AUG start codon, for example in polycistronic mRNA. See generally, Miles et al., U.S. Pat. No. 5,738,985 and N. Sonenberg and K. Meerovitch, Enzyme 44: 278-91 (1990). Addition of an IRES between the coding sequences for the transgene product and the NIS permits the independent translation of either the transgene product or the NIS from a dicistronic or polycistronic transcript. IRES sequences can be obtained from a number of RNA viruses (e.g., picornaviruses, hepatitis A, B, and C viruses, and influenza viruses) and DNA viruses (e.g., adenovirus). IRES have also been reported in mRNAs from eukaryotic cells (Macejak and Sarnow, Nature 353: 90-94 (1991) and Jackson, Nature 353: 14015 (1991)). Viral IRES sequences are detailed in the following publications:

Coxsackievirus
Jenkins, O., J. Gen. Virol. 68: 1835-1848 (1987)
Iizuka, N. et al., Virology 156: 64-73 (1987)
Hughes et al., J. Gen. Virol. 70: 2943-2952 (1989)
Hepatitis A Virus
Cohen, J. I. et al., Proc. Natl. Acad. Sci. USA 84: 2497-2501 (1987)
Paul et al., Virus Res. 8: 153-171 (1987)
Poliovirus
Racaniello and Baltimore, Proc. Natl. Acad. Sci. USA 78: 4887-4891 (1981)
Stanway, G. et al., Proc. Natl. Acad. Sci. USA 81: 1539-1543 (1984)
Rhinovirus
Deuchler et al., Proc. Natl. Acad. Sci. USA 84: 2605-2609 (1984)
Leckie, G., Ph.D. thesis, University of Reading, UK
Skern, T. et al., Nucleic Acids Res. 13: 2111 (1985)
Bovine Enterovirus
Earle et al., J. Gen. Virol. 69: 253-263 (1988)
Enterovirus Type 70
Ryan, M. D. et al., J. Gen. Virol. 71: 2291-99 (1989)
Theiler's Murine Encephalomyelitis Virus
Ohara et al., Virology 164: 245 (1988)
Peaver et al., Virology 161: 1507 (1988)
Encephalomyocarditis Virus
Palmenberg et al., Nucl. Acids Res. 12, 2969-2985 (1984)
Bae et al., Virology 170, 282-287 (1989)
Hepatitis C. Virus
Inchauspe et al., Proc. Natl. Acad. Sci. USA 88: 10293 (1991)
Okamoto et al., Virology 188: 331-341 (1992)
Kato et al., Proc. Natl. Acad. Sci. USA 87: 9524-9528 (1990)
Influenza Virus
Fiers, W. et al., Supramol. Struct. Cell Biochem. (Suppl 5), 357 (1981)
Release of the NIS For an embodiment of the invention which utilizes a protease cleavable linker between the transgene in the sequence encoding the NIS, the invention permits a great deal of flexibility and discretion in terms of the choice of the protease cleavable linker peptide. The protease specificity of the linker is determined by the amino acid sequence of the linker. Specific amino acid sequences can be selected in order to determine which protease will cleave the linker; this is an important indication of the location of cleavage within the cell or following secretion from the cell and can have a major effect on the release of the NIS. The furin cleavage signal is ideal for cell-associated transgenes that are transported to the cell surface through the Golgi compartment. Cell surface receptors, such as the LDL receptor used for the treatment of hypercholesterolemia or chimeric T cell receptors used for retargeting T cells can therefore be marked using furin-cleavable peptides. For cytoplasmic proteins, it is necessary to use cleavage signals that are recognized by cytoplasmic proteases and to use peptides with appropriate hydrophilic/hydrophobic balance so that they can escape across the plasma membrane.

Proteases useful according to the invention are described in the following references: V. Y. H. Hook, *Proteolytic and cellular mechanisms in prohormone and proprotein processing*, R G Landes Company, Austin, Tex., USA (1998); N. M. Hooper et al., Biochem. J. 321: 265-279 (1997); Z. Werb, Cell 91: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thornberry et al., J. Biol. Chem. 272: 17907-17911 (1997). In addition, a variety of different intracellular proteases useful according to the invention and their recognition sequences are summarized in Table 1. While not intending to limit the scope of the invention, the following list describes several of the known proteases which might be targeted by the linker and their location in the cell.

Secretory Pathway (ER/Golgi/Secretory Granules)
Signal peptidase
Proprotein convertases of the subtilisin/kexin family (furin, PC1, PC2, PC4, PACE4, PC5, PC)
Proprotein convertases cleaving at hydrophobic residues (e.g., Leu, Phe, Val, or Met)
Proprotein convertases cleaving at small amino acid residues such as Ala or Thr
Proopiomelanocortin converting enzyme (PCE)
Chromaffin granule aspartic protease (CGAP)
Prohormone thiol protease
Carboxypeptidases (e.g., carboxypeptidase E/H, carboxypeptidase D and carboxypeptidase Z)
Aminopeptidases (e.g., arginine aminopeptidase, lysine aminopeptidase, aminopeptidase B)
Cytoplasm
Prolyl endopeptidase
Aminopeptidase N
Insulin degrading enzyme
Calpain
High molecular weight protease
Caspases 1, 2, 3, 4, 5, 6, 7, 8, and 9
Cell Surface/Pericellular Space
Aminopeptidase N
Puromycin sensitive aminopeptidase
Angiotensin converting enzyme
Pyroglutamyl peptidase II
Dipeptidyl peptidase IV
N-arginine dibasic convertase
Endopeptidase 24.15
Endopeptidase 24.16
Amyloid precursor protein secretases alpha, beta and gamma
Angiotensin converting enzyme secretase
TGF alpha secretase
TNF alpha secretase
FAS ligand secretase
TNF receptor-I and -II secretases
CD30 secretase
KL1 and KL2 secretases
IL6 receptor secretase
CD43, CD44 secretase
CD16-I and CD16-II secretases
L-selectin secretase
Folate receptor secretase
MMP 1, 2, 3, 7, 8, 9, 10, 11, 12, 13, 14, and 15
Urokinase plasminogen activator
Tissue plasminogen activator
Plasmin
Thrombin
BMP-1 (procollagen C-peptidase)
ADAM 1, 2, 3, 4, 5, 6, 7, 8, 9, 10, and 11
Granzymes A, B, C, D, E, F, G, and H An alternative to relying on cell-associated proteases is to use a sequence encoding a self- or auto-cleaving linker. An example of such a sequence is that of the foot and mouth disease virus (FMDV) 2A protease. This is a short polypeptide of 17 amino acids that cleaves the polyprotein of FMDV at the 2A/2B junction. The sequence of the FMDV 2A propeptide is NFDLLKLAGDVESNPGP (SEQ ID NO: 5), which can be encoded by a nucleic acid sequence comprising ttgaagctgaataattttaatcgtcctctgcatctttcgttgggtcctggt (SEQ ID NO: 6). The cleavage occurs at the C-terminus of the peptide at the final glycine-proline amino acid pair. Cleavage of FMDV 2A propeptide is independent of the presence of other FMDV sequences and can generate cleavage in the presence of heterologous sequences. Insertion of this sequence between two protein coding regions results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (P. deFelipe et al., Gene Therapy 6: 198-208 (1999)). Thus, instead of using a cleavage signal recognizable by a cell-associated protease, the self-cleaving FMDV 2A protease sequence can be employed to link the NIS to the therapeutic polypeptide, resulting in spontaneous release of the NIS from the therapeutic protein.

Ex Vivo

Figure 8:
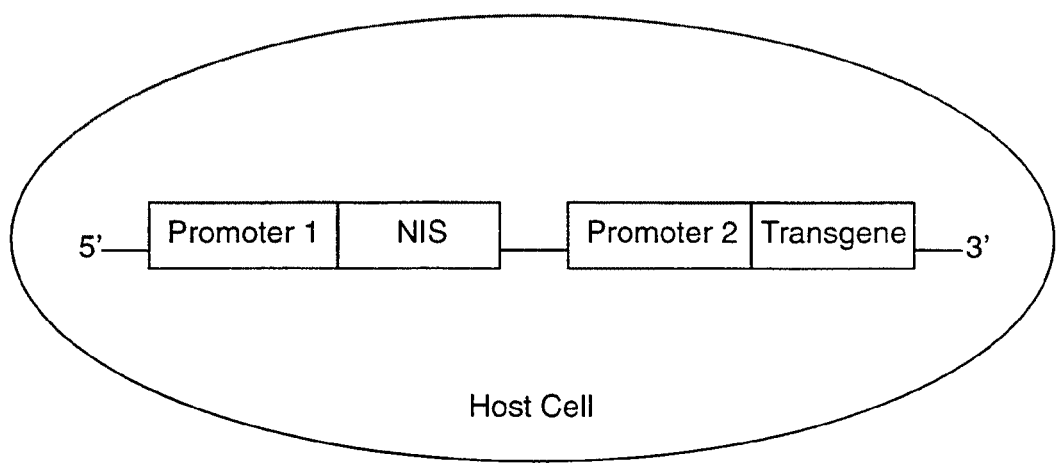
FIG. 8 displays a schematic representation of a host cell of the invention which contains a nucleic acid construct comprising a first promoter operably linked to a sequence encoding NIS at the 5' end of the construct and a second promoter operably linked to a transgene at the 3' end of the construct.
Figure 9:
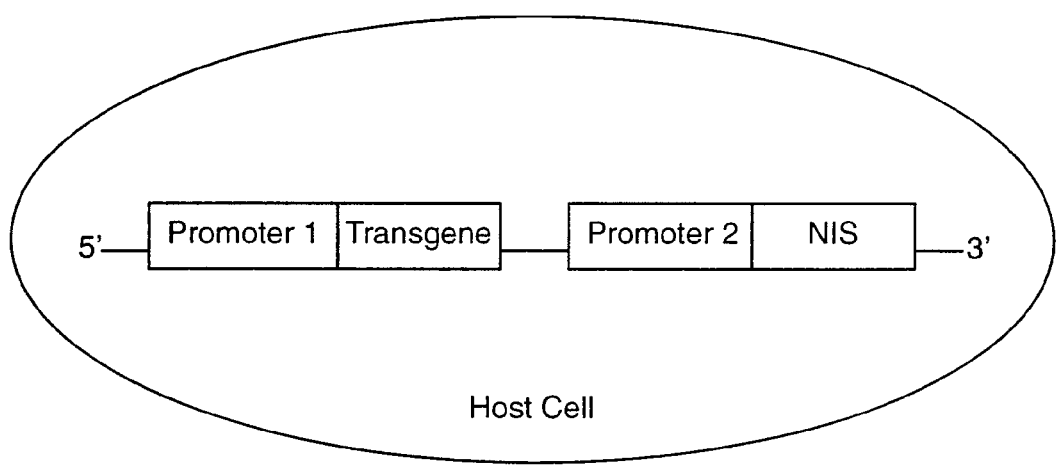
FIG. 9 displays a schematic representation of a host cell of the invention which contains a nucleic acid construct comprising a first promoter operably linked to a sequence encoding NIS at the 3' end of the construct and a second promoter operably linked to a transgene at the 5' end of the construct.

The above disclosure describes a method of determining transgene localization whereby the transgene is expressed as a fusion protein comprising the transgene product together with a NIS and a protease-cleavable linker peptide, or where the transgene is operable associated with a first promoter, while the sequence encoding the NIS is operably associated with a second promoter, or where the transgene and the sequence encoding the NIS are separated by a sequence encoding an IRES. With that method, the construct is used to transfect the cell, tissue, organ, or organism that is the target of gene therapy. The same nucleic acids can also be utilized in another fashion, whereby cells previously transfected with the nucleic acid (host cells; FIGS. 8 and 9) are transferred to a mammal, followed by administration of labeled iodine to visualize transgene localization. The host cell selected to receive the nucleic acid according to the invention may be found in situ within the mammalian recipient of the therapy, or the host cell can be a cell isolated from the mammal or from another source, and transfection with the nucleic acid can take place in vitro using standard techniques (e.g., the addition of calcium phosphate solutions or lipids known to induce transfection). The construct itself or a cell transfected in vitro with the construct can be introduced into the mammal by any suitable means known in the art, such as by injection, ingestion, or implantation.

In a variation of this embodiment, one or more cells that have been transfected with the nucleic acid construct described above is introduced to a mammal as a "marker cell" along with one or more cells which have been transfected with a nucleic acid construct comprising a nucleotide sequence which encodes the transgene, but not the NIS. The marker cell, accordingly, is used merely for monitoring the localization of the transgene and is present only in sufficient amount to transport iodine and detect the transported iodine. Where the marker cells for monitoring transgene localization are solely for monitoring purposes and not for treatment purposes, a cell(s) of the mammal (or from another source) is transfected in vitro using a vector described herein, containing both the transgene and the NIS gene (in any of the embodiments described herein), or a vector encoding only the NIS (FIGS. 10 and 11). Thus, cells administered for therapeutic purposes, i.e., containing a transgene, may comprise a small number of cells (i.e., 1%, 2%, 5%, 10%) containing both the transgene and the NIS gene, with the remaining large number of cells (90% or more) containing only the transgene. Alternatively a large proportion of cells (i.e., 60%, 75%, 90%, 100%) may contain both the transgene and the NIS gene, with the remaining cells (e.g. 40%, 25%, 10%) containing only the transgene.

The transfected marker cell(s) is introduced into the mammal concurrently with the introduction of cells transfected with a nucleic acid construct that encodes the transgene alone. Preferably, the marker cells carrying the construct of this invention are targeted to the same tissue or organ as cells carrying the therapeutic transgene for optimal localization of the therapeutic transgene. Expression of the NIS and subsequent sequestration of administered labeled iodine is used to determine the location of the transgene as described above The marker cells can alternatively be transfected with a construct that does not encode a protease-cleavable linker, but instead includes a second promoter which is associated with the sequence encoding the NIS. Another alternative is to transfect the marker cells with a construct that is transcribed to a polycistronic mRNA which comprises an internal ribosome entry site between the transgene and the sequence encoding the NIS. Because of the position of the ribosome entry site, both the transgene product and the NIS may be expressed separately without the need for protease cleavage.

Dosage and Mode of Administration

A nucleic acid according to the invention or a host cell containing the nucleic acid according to the invention may be administered in a pharmaceutical formulation, which comprises the nucleic acid or host cell mixed in a physiologically acceptable diluent such as water, phosphate buffered saline, or saline, and will exclude cell culture medium, particularly culture serum such as bovine serum or fetal calf serum, <0.5%. Administration may be intravenous, intraperitoneally, nasally, etc.

The dosage of nucleic acid according to the invention or cells containing the nucleic acid according to the invention will depend upon the disease indication and the route of administration, but should be generally between 1-1000 µg of DNA/kg of body weight/day or $10^3$-$10^9$ transfected cells/day. In embodiments comprising the administration of cells for therapeutic purposes, i.e., cells containing a transgene, the cells may comprise a small number (i.e., 1%, 2%, 5%, 10%) containing both the transgene and the NIS gene, or alternatively a large proportion of cells (i.e., 60%, 75%, 90%, 100%) containing both the transgene and the NIS gene. The dosage of nucleic acid, or cells containing nucleic acid encoding an NIS will be according to the same numerical guidelines provided above for a therapeutic nucleic acid or cell containing a therapeutic nucleic acid The duration of treatment will extend through the course of the disease symptoms and signs (clinical features), possibly continuously. Monitoring of NIS is performed at any time during the course of treatment. The number of doses will depend upon disease delivery vehicle and efficacy data from clinical trials. Symptoms for a given disease are indicated by the conventional clinical description of the disease, and will be selected for monitoring by the physician treating the disease. For example, the symptoms of cancer are well-known for each type of cancer. One clinical sign for cancer assessment, for example, is tumor size, which can be measured as an indicator of disease response to treatment. When clinical symptoms are assessed, the physician monitors the symptoms and evaluates whether the symptoms are getting worse or better as the disease progresses or recedes, respectively. One such example is monitoring the destruction of certain cell types that are malignant as an indicator of the success of treatment.

Kits

Another embodiment of the present invention is a kit containing a nucleic acid construct according to the invention and one or more reagents for the localization of the NIS, wherein the tissue distribution of the NIS is indicative of the distribution of the polypeptide encoded by the transgene. Reagents for detecting the NIS can include any detectable moiety complexed with iodine, such as radiolabeled iodine, wherein the use and distribution of the radiolabeled iodine complies with Federal radiation safety guidelines. An alternative kit would contain a cell according to the invention that has previously been transfected with the construct according to the invention together with one or more reagents for detection of the NIS. Either kit can include a set of instructions for using the construct or cell and for quantifying the NIS, for example, by SPECT or PET scanning.

Localization of the Transgene

The mammals are maintained on a low iodine diet for two weeks prior to the introduction of the nucleic acid construct by any of the methods described herein. A tracer dose of about 5-10 mCi, preferably about 1-5 mCi, and more preferably about 0.1-1 mCi of $^{131}$I, $^{124}$I, or $^{123}$I is administered by the intraperitoneal, or intravenous route at 24 hours, 48 hours, 96 hours, and 8 days following administration of the vector according to the invention. The syringe used to deliver the radioiodine is counted prior to and following iodine injection to verify the dose of radiation administered to the mammal. One hour after radioiodine injection, anterior and posterior images are taken using SPECT, or PET scans. Images according to the invention, may be taken of the whole body, or of specific regions, or organs. Image acquisition may be repeated at 2, 6 and 24 hours post-injection. Regions of uptake are mapped, and quantified (if using the PET method) and expressed as a fraction of the total amount of the administered radioiodine. Thus, detection of transported iodine as indicative of a transgene is that detection which the radiologist or physician determines qualitatively to be an image indicating transport of labeled iodine. The qualitative indication may be an area of the host body which is darker or denser in the scan, indicating sequestration of labeled iodine. Quantitative detection of transported labeled iodine indicative of the presence of a transgene is that percentage of the total labeled iodine administered that is above 1% and preferably about 10%.

Imaging with $^{124}$I PET will offer higher resolution imaging, higher sensitivity, attenuation correction, more accurate tumor localization and more accurate quantitation of uptake than is currently possible with conventional gamma cameras (Pentlow et al., *Medical Physics* 18: 357-366 (1991); Pentlow et al., *J. Nuc. Med.* 37: 1557-1562 (1996)) The physical characteristics of $^{124}$I including a half life of 4.2 days make it highly suitable for direct imaging of tissues capable of concentrating iodide, such as thyroid. Moreover, $^{124}$I is well suited for imaging of tissues which sequester iodine due to the expression of an exogenous NIS. Previous studies have demonstrated high resolution images and the ability to carefully quantitate iodide uptake and efflux by thyroid glands using this radionuclide (Crawford et al., *Eur. J. Nuc. Med.* 24: 1470-1478 (1997)) and positron emission tomography. Further, $^{124}$I PET has been shown to yield more accurate dosimetry measurements than conventional $^{131}$I (Ott et al., *Br. J. Radiol.* 60: 245-251 (1987); Flower et al., *Br. J. Radiol.* 63: 325-330 (1990); Flower et al., *Eur. J. Nuc. Med.* 21:531-536 (1994)). Potential for use of $^{124}$I to radioiodinate proteins such as antibodies or enzyme substrates and image their distribution to target tissues is also high, but has to date been investigated only in a small number of studies (Rubin et al. *Gyn Oncol.* 48:61-7, (1993); Arbit et al., *Eur J Nuc Med* 22:419-26, (1995); Tjuvajev et al. *Cancer Res.* 58:4333-41, (1998); Gambhir et al., *J Nuc Med.* 26:481-90, (1999)).

According to the present invention, $^{124}$I PET imaging will allow improved assessment of NIS activity and transgene distribution in mammals following administration of the nucleic acid construct bearing the transgene and a sequence encoding the NIS. In addition, $^{124}$I PET imaging permits more accurate dosimetry, which will allow optimization of the therapeutic responses. The techniques of both SPECT and PET are well described in the art, and are exemplified in the following references: Pentlow et al., *Medical Physics.* 18:357-66 (1991); Pentlow et al., *J Nuc Med.* 37:1557-62 (1996); Biegon, U.S. Pat. No. 5,304,367. The studies will also provide models of this technology for use in other tumor types and in other gene transfer experiments in which NIS is used as a therapeutic gene.

EXAMPLES

Example 1

Construction of Fusogenic Membrane Glycoproteins (FMG) Linked to NIS Expression Plasmids Expression plasmids were prepared with the nucleotide sequence encoding NIS linked to two different FMGs: gibbon ape leukemia virus (GALV; Delassus et al., *Virology* 173: 205-213, 1989) hyperfusogenic envelope lacking the cytoplasmic R-peptide and measles virus H glycoprotein (deStuart et al., *Lancet* 355: 201-202, 2000). Expression constructs were made using furin-cleavable or non-cleavable linkers to connect the 644 amino acid NIS to either the N-terminus of GALV (FIG. 6) or the C-terminus of Measles H glycoprotein (FIG. 7).

Example 2

In Vivo Gene Transfection Using Adenovirus

We have developed a replication-deficient human recombinant type 5 adenovirus (Ad5) carrying the human NIS gene linked to the CMV promoter (Ad5-CMV-NIS). LNCaP (human prostate cancer cell line) xenografts were established in nude mice and grown to approximately 5 mm diameter. Thereafter, 150 µL ($3 \times 10^{10}$ PFU in 3% sucrose/phosphate buffered saline) of Ad5-CMV-NIS (right flank) or control virus (left flank) was injected directly into the tumors using tuberculin syringes. The needle was moved to various sites within the tumor during injection to maximize the area of virus exposure. Four days following intratumoral injection of Ad5-CMV-NIS (right flank) or control virus (left flank), mice were injected intraperitoneally with of 500 µCi $^{123}$I and radioiodine imaging was performed using a gamma camera. Regions of uptake were quantified and expressed as a fraction of the total amount of the applied radioiodine. Iodide retention time within the tumor was determined by serial scanning following radioiodine injection, and dosimetric calculations were performed. Tumors were removed and evaluated for NIS expression by western blotting and by immunohistochemistry. In a second group of mice a single injection of 3 µCi $^{131}$I was given IP and the mice observed over time for therapeutic responses as described in section 10 above. Ad5-CMV-NIS transfected tumors readily trapped iodide and could be imaged with a gamma camera. The average uptake in 5 mice was 22.5±10.0% of the injected radioiodine dose. In contrast, tumors transfected with control virus constructs demonstrated no uptake of radioiodine and no image on the gamma camera. NIS protein expression was confirmed by western blotting and by immunohistochemistry.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

TABLE 1

Properties of some proteases associated with post-translational processing.

| Protease | Subcellular Localization | Tissue Distribution | Cleavage Signal | Nucleotide Sequence |
|---|---|---|---|---|
| furin | Golgi | ubiquitous | RXKR (SEQ ID NO: 7) | tctnnntttct (SEQ ID NO: 8) |
| MMP-2 | Golgi | tumor cells | PLGLWA (SEQ ID NO: 9) | cctaatcctaatacccgt (SEQ ID NO: 10) |
| MT1-MMP | plasma membrane | tumor cells | PLGLWA (SEQ ID NO: 11) | cctaatcctaatacccgt (SEQ ID NO: 12) |
| caspase-1 | secretory pathway | ubiquitous | YEVDGW (SEQ ID NO: 13) | atccttcatctgcctacc (SEQ ID NO: 14) |
| caspase-2 | | | VDVADGW (SEQ ID NO: 15) | catctgcatcgtctgcctacc (SEQ ID NO: 16) |
| caspase-3 | | | VDQMDGW (SEQ ID NO: 17) | catctggtttacctgcctacc (SEQ ID NO: 18) |
| caspase-4 | | | LEVDGW (SEQ ID NO: 19) | aatcttcatctgcctacc (SEQ ID NO: 20) |
| caspase-6 | | | VQVDGW (SEQ ID NO: 21) | catgttcatctgcctacc (SEQ ID NO: 22) |
| caspase-7 | | | VDQVDGW (SEQ ID NO: 23) | catctggttcatctgcctacc (SEQ ID NO: 24) |
| alpha-secretase | secretory pathway | ubiquitous | amyloid precursor protein (APP) | amyloid precursor protein (APP) |
| proprotein convertase (subtilisin/ kexin isozyme SKI-1) | endoplasmic reticulum | ubiquitous | brain neurotrophic growth factor precursor (RGLT (SEQ ID NO: 25)) | tctcctaattgt (SEQ ID NO: 26) |
| proprotein convertases (PC-2, PC-3, etc.) | secretory pathway | ubiquitous | | |
| tumor associated trypsin | | tumor cells | | |
| foot and mouth disease virus, protease 2A | | | NFDLLKLAGDVESNPGP (SEQ ID NO: 5) | ttgaagctgaataatttta atcgtcctctgcatctttc gttgggtcctggt (SEQ ID NO: 6) |

The invention claimed is:

1. A nucleic acid construct comprising a first promoter, a second promoter, a sequence encoding a fusogenic polypeptide, and a sequence encoding a sodium-iodide symporter, wherein said first promoter regulates expression of the sequence encoding said polypeptide, and wherein said second promoter regulates expression of the sequence encoding said sodium-iodide symporter.

2. The nucleic acid construct of claim 1, wherein said fusogenic polypeptide is a viral fusion protein.

3. The nucleic acid construct of claim 1, wherein said fusogenic polypeptide is a measles virus H glycoprotein.

4. The nucleic acid construct of claim 1, wherein said fusogenic polypeptide is a gibbon ape leukemia virus envelope glycoprotein.

5. A kit comprising:
(a) a nucleic acid construct or a cell transfected with said nucleic acid construct, wherein said nucleic acid construct comprising a first promoter, a second promoter, a sequence encoding a fusogenic polypeptide, and a sequence encoding a sodium-iodide symporter, wherein said first promoter regulates expression of the sequence encoding said fusogenic polypeptide, and wherein said second promoter regulates expression of the sequence encoding said sodium-iodide symporter, and
(b) a reagent for monitoring the location of said fusogenic polypeptide.

6. The kit of claim 5, wherein said reagent comprises labeled iodine or radioactive iodine.

* * * * *

UNITED STATES PATENT AND TRADEMARK OFFICE
CERTIFICATE OF CORRECTION

| | | |
|---|---|---|
| PATENT NO. | : 7,982,022 B2 | Page 1 of 1 |
| APPLICATION NO. | : 12/638435 | |
| DATED | : July 19, 2011 | |
| INVENTOR(S) | : Stephen James Russell | |

It is certified that error appears in the above-identified patent and that said Letters Patent is hereby corrected as shown below:

Title Page, References Cited, Other Publications, Stratagene Catalog reference, please delete "Stratage" and insert --Stratagene-- therefor;

Title Page, References Cited, Other Publications, Appelos et al. reference, please delete "Appelos" and insert --Appelros-- therefor;

Column 1, line 7, please delete "as" and insert --is-- therefor;

Column 1, line 10, please delete "6,586,411, )" and insert --6,586,411),-- therefor.

Signed and Sealed this
Twenty-fifth Day of October, 2011

David J. Kappos
*Director of the United States Patent and Trademark Office*

SEQUENCE LISTING

<160> NUMBER OF SEQ ID NOS: 34

<210> SEQ ID NO 1
<211> LENGTH: 1932
<212> TYPE: DNA
<213> ORGANISM: Homo Sapiens

<400> SEQUENCE: 1
atggaggccg tggagaccgg ggaacggccc accttcggag cctgggacta cggggtcttt     60
gccctcatgc tcctggtgtc cactggcatc gggctgtggg tcgggctggc tcggggcggg    120

```
cagcgcagcg ctgaggactt cttcaccggg ggccggcgcc tggcggccct gcccgtgggc    180
ctgtcgctgt ctgccagctt catgtcggcc gtgcaggtgc tgggcgtgcc gtcggaggcc    240
tatcgctatg ccctcaagtt cctctggatg tgcctgggcc agcttctgaa ctcggtcctc    300
accgccctgc tcttcatgcc cgtcttctac cgcctgggcc tcaccagcac ctacgagtac    360
ctggagatgc gcttcagccg cgcagtgcgg ctctgcggga cttttgcagta cattgtagcc    420 acgatgctgt acaccggcat cgtaatctac gcaccggccc tcatcctgaa ccaagtgacc    480
gggctggaca tctgggcgtc gctcctgtcc accggaatta tctgcacctt ctacacggct    540
gtgggcggca tgaaggctgt ggtctggact gatgtgttcc aggtcgtggt gatgctaagt    600
ggcttctggg ttgtcctggc acgcggtgtc atgcttgtgg gcgggccccg ccaggtgctc    660
acgctggccc agaaccactc ccggatcaac ctcatggact ttaaccctga cccgaggagc    720
cgctatacat tctggacttt tgtggtgggt ggcacgttgg tgtggctctc catgtatggc    780
gtgaaccagg cgcaggtgca cgctacgtg gcttgccgca cagagaagca ggccaagctg    840
gccctgctca tcaaccaggt cggcctgttc ctgatcgtgt ccagcgctgc ctgctgtggc    900
atcgtcatgt ttgtgttcta cactgactgc gaccctctcc tcctggggcg catctctgcc    960
ccagaccagt acatgcctct gctggtgctg gacatcttcg aagatctgcc tggagtcccc   1020 gggctttttcc tggcctgtgc ttacagtggc accctcagca cagcatccac cagcatcaat   1080
gctatggctg cagtcactgt agaagacctc atcaaacctc ggctgcggag cctggcaccc   1140
aggaaactcg tgattatctc caaggggctc tcactcatct acggatcggc ctgtctcacc   1200
gtggcagccc tgtcctcact gctcggagga ggtgtccttc agggctcctt caccgtcatg   1260
ggagtcatca gcggcccccct gctgggagcc ttcatcttgg gaatgttcct gccggcctgc   1320
aacacaccgg gcgtcctcgc gggactaggc gcgggcttgg cgctgtcgct gtgggtggcc   1380
ttgggcgcca cgctgtaccc acccagcgag cagaccatga gggtcctgcc atcgtcggct   1440
gcccgctgcg tggctctctc agtcaacgcc tctggcctcc tggacccggc tctcctccct   1500
gctaacgact ccagcagggc ccccagctca ggaatggacg ccagccgacc cgccttagct   1560
gacagcttct atgccatctc ctatctctat tacggtgccc tgggcacgct gaccactgtg   1620
ctgtgcggag ccctcatcag ctgcctgaca ggccccacca agcgcagcac cctgccccg   1680 ggattgttgt ggtgggacct cgcacggcag acagcatcag tggcccccaa ggaagaagtg   1740
gccatcctgg atgacaactt ggtcaaggtt cctgaagaac tccccactgg aaacaagaag   1800 cccccctggct tcctgcccac caatgaggat cgtctgtttt cttggggca aaggagctg    1860 gaggggctg gctcttggac cccctgtgtt ggacatgatg gtggtcgaga ccagcaggag   1920
acaaacctct ga                                                        1932
```

<210> SEQ ID NO 2
<211> LENGTH: 643
<212> TYPE: PRT
<213> ORGANISM: Homo Sapiens

<400> SEQUENCE: 2

Met Glu Ala Val Glu Thr Gly Glu Arg Pro Thr Phe Gly Ala Trp Asp
1               5                   10                  15

Tyr Gly Val Phe Ala Leu Met Leu Leu Val Ser Thr Gly Ile Gly Leu
                20                  25                  30

Trp Val Gly Leu Ala Arg Gly Gly Gln Arg Ser Ala Glu Asp Phe Phe
            35                  40                  45

-continued

```
Thr Gly Gly Arg Arg Leu Ala Ala Leu Pro Val Gly Leu Ser Leu Ser
     50                  55                  60

Ala Ser Phe Met Ser Ala Val Gln Val Leu Gly Val Pro Ser Glu Ala
 65              70                  75                  80

Tyr Arg Tyr Gly Leu Lys Phe Leu Trp Met Cys Leu Gly Gln Leu Leu
                 85                  90                  95

Asn Ser Val Leu Thr Ala Leu Leu Phe Met Pro Val Phe Tyr Arg Leu
             100                 105                 110

Gly Leu Thr Ser Thr Tyr Glu Tyr Leu Glu Met Arg Phe Ser Arg Ala
             115                 120                 125

Val Arg Leu Cys Gly Thr Leu Gln Tyr Ile Val Ala Thr Met Leu Tyr
         130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                 165                 170                 175

Phe Tyr Thr Ala Val Gly Gly Met Lys Ala Val Trp Thr Asp Val
             180                 185                 190

Phe Gln Val Val Met Leu Ser Gly Phe Trp Val Val Leu Ala Arg
         195                 200                 205

Gly Val Met Leu Val Gly Pro Arg Gln Val Leu Thr Leu Ala Gln
     210                 215                 220

Asn His Ser Arg Ile Asn Leu Met Asp Phe Asn Pro Asp Pro Arg Ser
225                 230                 235                 240

Arg Tyr Thr Phe Trp Thr Phe Val Val Gly Gly Thr Leu Val Trp Leu
                 245                 250                 255

Ser Met Tyr Gly Val Asn Gln Ala Gln Val Gln Arg Tyr Val Ala Cys
             260                 265                 270

Arg Thr Glu Lys Gln Ala Lys Leu Ala Leu Leu Ile Asn Gln Val Gly
         275                 280                 285

Leu Phe Leu Ile Val Ser Ser Ala Ala Cys Cys Gly Ile Val Met Phe
     290                 295                 300

Val Phe Tyr Thr Asp Cys Asp Pro Leu Leu Gly Arg Ile Ser Ala
305                 310                 315                 320

Pro Asp Gln Tyr Met Pro Leu Leu Val Leu Asp Ile Phe Glu Asp Leu
                 325                 330                 335

Pro Gly Val Pro Gly Leu Phe Leu Ala Cys Ala Tyr Ser Gly Thr Leu
             340                 345                 350

Ser Thr Ala Ser Thr Ser Ile Asn Ala Met Ala Ala Val Thr Val Glu
         355                 360                 365

Asp Leu Ile Lys Pro Arg Leu Arg Ser Leu Ala Pro Arg Lys Leu Val
     370                 375                 380

Ile Ile Ser Lys Gly Leu Ser Leu Ile Tyr Gly Ser Ala Cys Leu Thr
385                 390                 395                 400

Val Ala Ala Leu Ser Ser Leu Leu Gly Gly Val Leu Gln Gly Ser
                 405                 410                 415

Phe Thr Val Met Gly Val Ile Ser Gly Pro Leu Leu Gly Ala Phe Ile
             420                 425                 430

Leu Gly Met Phe Leu Pro Ala Cys Asn Thr Pro Gly Val Leu Ala Gly
         435                 440                 445

Leu Gly Ala Gly Leu Ala Leu Ser Leu Trp Val Ala Leu Gly Ala Thr
     450                 455                 460

Leu Tyr Pro Pro Ser Glu Gln Thr Met Arg Val Leu Pro Ser Ser Ala
465                 470                 475                 480
```

```
Ala Arg Cys Val Ala Leu Ser Val Asn Ala Ser Gly Leu Leu Asp Pro
            485                 490                 495

Ala Leu Leu Pro Ala Asn Asp Ser Ser Arg Ala Pro Ser Ser Gly Met
        500                 505                 510

Asp Ala Ser Arg Pro Ala Leu Ala Asp Ser Phe Tyr Ala Ile Ser Tyr
            515                 520                 525

Leu Tyr Tyr Gly Ala Leu Gly Thr Leu Thr Val Leu Cys Gly Ala
        530                 535                 540

Leu Ile Ser Cys Leu Thr Gly Pro Thr Lys Arg Ser Thr Leu Ala Pro
545                 550                 555                 560

Gly Leu Leu Trp Trp Asp Leu Ala Arg Gln Thr Ala Ser Val Ala Pro
                565                 570                 575

Lys Glu Glu Val Ala Ile Leu Asp Asp Asn Leu Val Lys Gly Pro Glu
            580                 585                 590

Glu Leu Pro Thr Gly Asn Lys Lys Pro Pro Gly Phe Leu Pro Thr Asn
        595                 600                 605

Glu Asp Arg Leu Phe Phe Leu Gly Gln Lys Glu Leu Glu Gly Ala Gly
    610                 615                 620

Ser Trp Thr Pro Cys Val Gly His Asp Gly Gly Arg Asp Gln Gln Glu
625                 630                 635                 640

Thr Asn Leu

<210> SEQ ID NO 3
<211> LENGTH: 1857
<212> TYPE: DNA
<213> ORGANISM: Rattus sp.

<400> SEQUENCE: 3 atggaggtg cggaggccgg ggcccgggcc accttcggcg cctgggacta cggcgtgttc     60
gcgaccatgc tgctggtgtc cacgggcatc gggctatggg tcggcctggc ccgcggtggc    120
caacgcagtg ccgacgactt cttttaccgg ggccggcagt tggcagccgt tcctgtgggg    180
ctgtcgctgg ccgccagttt catgtcggct gtgcaggtgc tcggggtccc cgccgaggca    240
gcgcgctacg ggctcaagtt cctgtggatg tgcgcgggtc agttgctcaa ctcgctgctc    300
acagcgtttc tcttcttgcc gatcttctac cgcctgggcc ttaccagcac ctaccagtac    360
ctagagctgc gcttcagccg agcggtccgg ctctgcggga cgctgcagta cttggtggcc    420
acgatgctgt ataggcat cgtgatctac gcgcctgcgc tcatcctgaa ccaagtgacc    480
gggttggaca tctgggcatc gctcctgtcc acaggaatca tctgcacctt gtacactacc    540
gtgggtggta tgaaggccgt ggtctggaca gatgtgttcc aggttgtggt aatgctcgtt    600
ggcttctggg tgatcctggc ccgaggcgtc attctcctgg ggggtccccg gaacgtgctc    660
agcctcgctc agaaccattc ccggatcaac ctgatggact tgaccctga tcctcggagc    720 cggtacaccct tctggacttt catagtgggt ggcacactgt gtggctctc catgtacggt    780 gtgaaccaag cccaggtaca gcgctatgtg gcctgccaca cagagggaaa ggccaaactg    840
gccctgcttg tcaaccagct gggcctcttc ctgattgtgg ccagtgcagc ttgctgtggc    900
attgtcatgt tcgtctacta caaggactgt gaccccctcc tcacaggccg tatctcagcc    960
cccgaccagt acatgccgct gcttgtgttg acattttgt aggatctgcc cggggtcccc   1020
gggctcttcc tggcctgtgc ctacagtggc accctcagca ctgcatccac cagcatcaac   1080
gccatggcag ctgtgactgt ggaagacctc atcaagccga ggatgcctgg cctggcacct   1140
cggaagttgg ttttcatctc taaagggctc tcattcatct acggctctgc ctgcctcact   1200
```

```
gtggctgctc tgtcctcact gctgggaggt ggtgtcctcc agggttcctt cactgtgatg      1260
ggtgtcatca gtgggcctct actaggcgcc ttcacgcttg ggatgctgct cccagcctgc      1320
aacacgccag gcgttctctc cgggttggca gcaggcttgg ctgtatccct gtgggtggcc      1380
gtaggggcca cactgtatcc ccctggagag cagaccatgg gggtgctgcc cacctcggct      1440
gcaggctgca ccaacgattc ggtcctcctg gcccaccctg gagccaccaa cgcttccaac      1500
gggatcccca gttctggaat ggacacgggc cgccctgccc tcgctgatac cttttacgcc      1560
atctcctatc tctattacgg ggctctgggc acgctgacca ccatgctttg cggtgctctc      1620
atcagctacc ttactggtcc caccaagcgc agctccctgg gtcccggatt gctgtggtgg      1680
gaccttgctc gacagacagc gtctgtggcc ccaaaggaag acactgccac cctggaggag      1740
agcctggtga agggaccgga agacatccct gctgtgacca agaagccccc tggcctcaag      1800
ccaggcgccg agaccaccc cctgtatctg gggcacgatg tggagaccaa cctctga        1857
```

```
<210> SEQ ID NO 4
<211> LENGTH: 618
<212> TYPE: PRT
<213> ORGANISM: Rattus sp.

<400> SEQUENCE: 4

Met Glu Gly Ala Glu Ala Gly Ala Arg Ala Thr Phe Gly Ala Trp Asp
1               5                   10                  15

Tyr Gly Val Phe Ala Thr Met Leu Leu Val Ser Thr Gly Ile Gly Leu
                20                  25                  30

Trp Val Gly Leu Ala Arg Gly Gly Gln Arg Ser Ala Asp Asp Phe Phe
            35                  40                  45

Thr Gly Gly Arg Gln Leu Ala Ala Val Pro Val Gly Leu Ser Leu Ala
        50                  55                  60

Ala Ser Phe Met Ser Ala Val Gln Val Leu Gly Val Pro Ala Glu Ala
65                  70                  75                  80

Ala Arg Tyr Gly Leu Lys Phe Leu Trp Met Cys Ala Gly Gln Leu Leu
                85                  90                  95

Asn Ser Leu Leu Thr Ala Phe Leu Phe Leu Pro Ile Phe Tyr Arg Leu
            100                 105                 110

Gly Leu Thr Ser Thr Tyr Gln Tyr Leu Glu Leu Arg Phe Ser Arg Ala
        115                 120                 125

Val Arg Leu Cys Gly Thr Leu Gln Tyr Leu Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                165                 170                 175

Leu Tyr Thr Thr Val Gly Gly Met Lys Ala Val Val Trp Thr Asp Val
            180                 185                 190

Phe Gln Val Val Val Met Leu Val Gly Phe Trp Val Ile Leu Ala Arg
        195                 200                 205

Gly Val Ile Leu Leu Gly Gly Pro Arg Asn Val Leu Ser Leu Ala Gln
    210                 215                 220

Asn His Ser Arg Ile Asn Leu Met Asp Phe Asp Pro Asp Pro Arg Ser
225                 230                 235                 240

Arg Tyr Thr Phe Trp Thr Phe Ile Val Gly Gly Thr Leu Val Trp Leu
                245                 250                 255

Ser Met Tyr Gly Val Asn Gln Ala Gln Val Gln Arg Tyr Val Ala Cys
```

```
                260                 265                 270
His Thr Glu Gly Lys Ala Lys Leu Ala Leu Leu Val Asn Gln Leu Gly
            275                 280                 285

Leu Phe Leu Ile Val Ala Ser Ala Ala Cys Cys Gly Ile Val Met Phe
        290                 295                 300

Val Tyr Tyr Lys Asp Cys Asp Pro Leu Leu Thr Gly Arg Ile Ser Ala
305                 310                 315                 320

Pro Asp Gln Tyr Met Pro Leu Val Leu Asp Ile Phe Glu Asp Leu
                325                 330                 335

Pro Gly Val Pro Gly Leu Phe Leu Ala Cys Ala Tyr Ser Gly Thr Leu
            340                 345                 350

Ser Thr Ala Ser Thr Ser Ile Asn Ala Met Ala Ala Val Thr Val Glu
            355                 360                 365

Asp Leu Ile Lys Pro Arg Met Pro Gly Leu Ala Pro Arg Lys Leu Val
        370                 375                 380

Phe Ile Ser Lys Gly Leu Ser Phe Ile Tyr Gly Ser Ala Cys Leu Thr
385                 390                 395                 400

Val Ala Ala Leu Ser Ser Leu Leu Gly Gly Val Leu Gln Gly Ser
            405                 410                 415

Phe Thr Val Met Gly Val Ile Ser Gly Pro Leu Leu Gly Ala Phe Thr
                420                 425                 430

Leu Gly Met Leu Leu Pro Ala Cys Asn Thr Pro Gly Val Leu Ser Gly
            435                 440                 445

Leu Ala Ala Gly Leu Ala Val Ser Leu Trp Val Ala Val Gly Ala Thr
        450                 455                 460

Leu Tyr Pro Pro Gly Glu Gln Thr Met Gly Val Leu Pro Thr Ser Ala
465                 470                 475                 480

Ala Gly Cys Thr Asn Asp Ser Val Leu Leu Gly Pro Pro Gly Ala Thr
                485                 490                 495

Asn Ala Ser Asn Gly Ile Pro Ser Ser Gly Met Asp Thr Gly Arg Pro
            500                 505                 510

Ala Leu Ala Asp Thr Phe Tyr Ala Ile Ser Tyr Leu Tyr Tyr Gly Ala
        515                 520                 525

Leu Gly Thr Leu Thr Thr Met Leu Cys Gly Ala Leu Ile Ser Tyr Leu
530                 535                 540

Thr Gly Pro Thr Lys Arg Ser Ser Leu Gly Pro Gly Leu Leu Trp Trp
545                 550                 555                 560

Asp Leu Ala Arg Gln Thr Ala Ser Val Ala Pro Lys Glu Asp Thr Ala
                565                 570                 575

Thr Leu Glu Glu Ser Leu Val Lys Gly Pro Glu Asp Ile Pro Ala Val
            580                 585                 590

Thr Lys Lys Pro Pro Gly Leu Lys Pro Gly Ala Glu Thr His Pro Leu
        595                 600                 605

Tyr Leu Gly His Asp Val Glu Thr Asn Leu
610                 615

<210> SEQ ID NO 5
<211> LENGTH: 17
<212> TYPE: PRT
<213> ORGANISM: Foot-and-mouth disease virus

<400> SEQUENCE: 5

Asn Phe Asp Leu Leu Lys Leu Ala Gly Asp Val Glu Ser Asn Pro Gly
1               5                   10                  15

Pro
```

```
<210> SEQ ID NO 6
<211> LENGTH: 51
<212> TYPE: DNA
<213> ORGANISM: Foot-and-mouth disease virus

<400> SEQUENCE: 6
ttgaagctga ataattttaa tcgtcctctg catctttcgt tgggtcctgg t          51

<210> SEQ ID NO 7
<211> LENGTH: 4
<212> TYPE: PRT
<213> ORGANISM: Homo Sapiens
<220> FEATURE:
<221> NAME/KEY: VARIANT
<222> LOCATION: 2
<223> OTHER INFORMATION: Xaa = Any Amino Acid

<400> SEQUENCE: 7

Arg Xaa Lys Arg
1

<210> SEQ ID NO 8
<211> LENGTH: 12
<212> TYPE: DNA
<213> ORGANISM: Homo Sapiens
<220> FEATURE:
<221> NAME/KEY: misc_feature
<222> LOCATION: 4; 5; 6
<223> OTHER INFORMATION: n = A,T,C or G

<400> SEQUENCE: 8
tctnnntttt ct                                                     12

<210> SEQ ID NO 9
<211> LENGTH: 6
<212> TYPE: PRT
<213> ORGANISM: Homo Sapiens

<400> SEQUENCE: 9

Pro Leu Gly Leu Trp Ala
1               5

<210> SEQ ID NO 10
<211> LENGTH: 18
<212> TYPE: DNA
<213> ORGANISM: Homo Sapiens

<400> SEQUENCE: 10
cctaatccta atacccgt                                               18

<210> SEQ ID NO 11
<211> LENGTH: 6
<212> TYPE: PRT
<213> ORGANISM: Homo Sapiens

<400> SEQUENCE: 11

Pro Leu Gly Leu Trp Ala
1               5

<210> SEQ ID NO 12
<211> LENGTH: 18
<212> TYPE: DNA
<213> ORGANISM: Homo Sapiens

<400> SEQUENCE: 12
```

```
cctaatccta atacccgt                                              18
```

<210> SEQ ID NO 13
<211> LENGTH: 6
<212> TYPE: PRT
<213> ORGANISM: Homo Sapiens

<400> SEQUENCE: 13

Tyr Glu Val Asp Gly Trp
1               5

<210> SEQ ID NO 14
<211> LENGTH: 18
<212> TYPE: DNA
<213> ORGANISM: Homo Sapiens

<400> SEQUENCE: 14

```
atccttcatc tgcctacc                                              18
```

<210> SEQ ID NO 15
<211> LENGTH: 7
<212> TYPE: PRT
<213> ORGANISM: Homo Sapiens

<400> SEQUENCE: 15

Val Asp Val Ala Asp Gly Trp
1               5

<210> SEQ ID NO 16
<211> LENGTH: 21
<212> TYPE: DNA
<213> ORGANISM: Homo Sapiens

<400> SEQUENCE: 16

```
catctgcatc gtctgcctac c                                          21
```

<210> SEQ ID NO 17
<211> LENGTH: 7
<212> TYPE: PRT
<213> ORGANISM: Homo Sapiens

<400> SEQUENCE: 17

Val Asp Gln Met Asp Gly Trp
1               5

<210> SEQ ID NO 18
<211> LENGTH: 21
<212> TYPE: DNA
<213> ORGANISM: Homo Sapiens

<400> SEQUENCE: 18

```
catctggttt acctgcctac c                                          21
```

<210> SEQ ID NO 19
<211> LENGTH: 6
<212> TYPE: PRT
<213> ORGANISM: Homo Sapiens

<400> SEQUENCE: 19

Leu Glu Val Asp Gly Trp
1               5

<210> SEQ ID NO 20
<211> LENGTH: 18
<212> TYPE: DNA

```
<213> ORGANISM: Homo Sapiens

<400> SEQUENCE: 20
aatcttcatc tgcctacc                                                      18

<210> SEQ ID NO 21
<211> LENGTH: 6
<212> TYPE: PRT
<213> ORGANISM: Homo Sapiens

<400> SEQUENCE: 21

Val Gln Val Asp Gly Trp
1               5

<210> SEQ ID NO 22
<211> LENGTH: 18
<212> TYPE: DNA
<213> ORGANISM: Homo Sapiens

<400> SEQUENCE: 22
catgttcatc tgcctacc                                                      18

<210> SEQ ID NO 23
<211> LENGTH: 7
<212> TYPE: PRT
<213> ORGANISM: Homo Sapiens

<400> SEQUENCE: 23

Val Asp Gln Val Asp Gly Trp
1               5

<210> SEQ ID NO 24
<211> LENGTH: 21
<212> TYPE: DNA
<213> ORGANISM: Homo Sapiens

<400> SEQUENCE: 24
catctggttc atctgcctac c                                                  21

<210> SEQ ID NO 25
<211> LENGTH: 4
<212> TYPE: PRT
<213> ORGANISM: Homo Sapiens

<400> SEQUENCE: 25

Arg Gly Leu Thr
1

<210> SEQ ID NO 26
<211> LENGTH: 12
<212> TYPE: DNA
<213> ORGANISM: Homo Sapiens

<400> SEQUENCE: 26
tctcctaatt gt                                                            12

<210> SEQ ID NO 27
<211> LENGTH: 7
<212> TYPE: PRT
<213> ORGANISM: Unknown
<220> FEATURE:
<223> OTHER INFORMATION: Furin cleavage site

<400> SEQUENCE: 27

Arg Leu Lys Arg Gly Ser Arg
```

```
<210> SEQ ID NO 28
<211> LENGTH: 4
<212> TYPE: PRT
<213> ORGANISM: Unknown
<220> FEATURE:
<223> OTHER INFORMATION: Factor Xa Cleavage Site

<400> SEQUENCE: 28

Ile Glu Gly Arg
1

<210> SEQ ID NO 29
<211> LENGTH: 5
<212> TYPE: PRT
<213> ORGANISM: Gibbon Ape Leukemia Virus

<400> SEQUENCE: 29

Ser Leu Gln Asn Lys
1               5

<210> SEQ ID NO 30
<211> LENGTH: 6
<212> TYPE: PRT
<213> ORGANISM: Measles Virus

<400> SEQUENCE: 30

Arg Glu Asp Gly Thr Asn
1               5

<210> SEQ ID NO 31
<211> LENGTH: 7
<212> TYPE: PRT
<213> ORGANISM: Streptomyces fimbriatus

<400> SEQUENCE: 31

Ala Ala Gln Pro Ala Ala Ala
1               5

<210> SEQ ID NO 32
<211> LENGTH: 5
<212> TYPE: PRT
<213> ORGANISM: Streptomyces fimbriatus

<400> SEQUENCE: 32

Ala Ala Gln Pro Ala
1               5

<210> SEQ ID NO 33
<211> LENGTH: 4
<212> TYPE: PRT
<213> ORGANISM: Unknown
<220> FEATURE:
<223> OTHER INFORMATION: Cleavable Linker Site

<400> SEQUENCE: 33

Arg Leu Lys Arg
1

<210> SEQ ID NO 34
<211> LENGTH: 5
<212> TYPE: PRT
<213> ORGANISM: Unknown
<220> FEATURE:
<223> OTHER INFORMATION: Non-Cleavable Linker Site
```

```
<400> SEQUENCE: 34

Gly Gly Gly Gly Ser
1               5
```